(12) United States Patent
Gyde et al.

(10) Patent No.: US 12,409,474 B2
(45) Date of Patent: Sep. 9, 2025

(54) DEVICES FOR ANALYSIS OF A FLUID

(71) Applicant: S.C.R. (ENGINEERS) LIMITED, Netanya (IL)

(72) Inventors: Dwayne Mark Gyde, Hamilton (NZ); Paul David Harris, Hamilton (NZ); Robert Graham Orchard, Hamilton (NZ); Samuel James Whetnall, Hamilton (NZ)

(73) Assignee: S.C.R. (ENGINEERS) LIMITED, Netanya (IL)

( * ) Notice: Subject to any disclaimer, the term of this patent is extended or adjusted under 35 U.S.C. 154(b) by 866 days.

(21) Appl. No.: 17/638,828

(22) PCT Filed: Aug. 28, 2020

(86) PCT No.: PCT/NZ2020/050095
§ 371 (c)(1),
(2) Date: Feb. 27, 2022

(87) PCT Pub. No.: WO2021/040540
PCT Pub. Date: Mar. 4, 2021

(65) Prior Publication Data
US 2022/0323995 A1    Oct. 13, 2022

(30) Foreign Application Priority Data
Aug. 28, 2019    (NZ) .......................... 756776

(51) Int. Cl.
*B06B 1/06* (2006.01)
*G01N 29/028* (2006.01)
(Continued)

(52) U.S. Cl.
CPC ............ *B06B 1/0677* (2013.01); *B06B 1/067* (2013.01); *G01N 29/028* (2013.01);
(Continued)

(58) Field of Classification Search
CPC ..... B06B 1/0677; B06B 1/067; B06B 1/0215; B06B 1/0644; B06B 2201/70; B06B 3/02;
(Continued)

(56) References Cited

U.S. PATENT DOCUMENTS

| 85,575 A | 1/1869 | Drake |
|---|---|---|
| 377,588 A | 2/1888 | Walsh, Jr. |

(Continued)

FOREIGN PATENT DOCUMENTS

| AU | 199534570 | 10/1994 |
|---|---|---|
| AU | 2003239832 | 5/2002 |

(Continued)

OTHER PUBLICATIONS

Christian Pahl, Eberhard Hartung, Anne Grothmann, Katrin Mahlkow-Nerge, Angelika Haeussermann, Rumination activity of dairy cows in the 24 hours before and after calving, Journal of Dairy Science, vol. 97, Issue 11, 2014, pp. 6935-6941.

(Continued)

*Primary Examiner* — Emily P Pham
(74) *Attorney, Agent, or Firm* — Keith O'Doherty

(57) ABSTRACT

An ultrasonic transducer is described, including a piezoelectric element, a fluid medium contact layer, a matching layer between the piezoelectric element and the fluid medium contact layer, and a backing layer. Ultrasound sensor devices utilising the ultrasonic transducer are also described, for use in systems for analysing a fluid such as milk.

26 Claims, 6 Drawing Sheets

(51) Int. Cl.
*G01N 29/036* (2006.01)
*G01N 29/22* (2006.01)
*G01N 29/24* (2006.01)

(52) U.S. Cl.
CPC ......... *G01N 29/036* (2013.01); *G01N 29/222* (2013.01); *G01N 29/245* (2013.01)

(58) Field of Classification Search
CPC .. G01N 29/028; G01N 29/036; G01N 29/222; G01N 29/245; G01N 29/2437; G01N 29/4436; G01N 29/348; G01N 2291/102; G01N 2291/0228; G01N 2291/02466; G01N 2291/02818; G01N 33/04; G01H 3/00; G01H 11/08
See application file for complete search history.

(56) References Cited

U.S. PATENT DOCUMENTS

| | | | |
|---|---|---|---|
| 584,121 A | 6/1897 | Sanders | |
| 818,783 A | 4/1906 | Philippi | |
| 823,079 A | 6/1906 | Rais | |
| 1,016,752 A | 2/1912 | Leith | |
| 1,188,510 A | 6/1916 | Timson | |
| 1,364,137 A | 1/1921 | Pannier | |
| 1,759,400 A | 5/1930 | Hobbs | |
| 1,843,314 A | 2/1932 | Berntson et al. | |
| 1,863,037 A | 6/1932 | Archbold | |
| 2,078,827 A | 4/1937 | Ketchum | |
| 2,420,020 A | 5/1947 | Snell | |
| 2,553,400 A | 5/1951 | Blair | |
| 2,570,048 A | 10/1951 | Cooke et al. | |
| 3,091,770 A | 6/1963 | McMurray et al. | |
| 3,261,243 A | 7/1966 | Ellison | |
| 3,596,541 A | 8/1971 | Bieganski | |
| 3,812,859 A | 5/1974 | Murphy et al. | |
| 3,884,100 A | 5/1975 | Fideldy | |
| 3,981,209 A | 9/1976 | Caroff | |
| 4,120,303 A | 10/1978 | Villa-Massone et al. | |
| 4,121,591 A | 10/1978 | Hayes | |
| 4,281,657 A | 8/1981 | Ritchey | |
| 4,323,183 A | 4/1982 | Duchin | |
| 4,497,321 A | 2/1985 | Fearing et al. | |
| 4,516,577 A | 5/1985 | Scott et al. | |
| 4,531,520 A | 7/1985 | Reggers et al. | |
| 4,552,147 A | 11/1985 | Gardner | |
| 4,666,436 A | 5/1987 | McDonald et al. | |
| 4,672,966 A | 6/1987 | Haas, Jr. | |
| 4,696,119 A | 9/1987 | Howe et al. | |
| 4,716,899 A | 1/1988 | Huenefeld et al. | |
| 4,819,639 A | 4/1989 | Gardner | |
| 4,821,683 A | 4/1989 | Veldman | |
| 4,943,294 A | 7/1990 | Knapp | |
| 5,022,253 A | 6/1991 | Parlatore | |
| 5,056,385 A | 10/1991 | Petersen | |
| 5,141,514 A | 8/1992 | van Amelsfort | |
| 5,154,721 A | 10/1992 | Perez | |
| 5,267,464 A | 12/1993 | Cleland | |
| 5,297,553 A | 3/1994 | Sliwa, Jr. et al. | |
| 5,509,291 A | 4/1996 | Nilsson et al. | |
| 5,651,791 A | 7/1997 | Zavlodaver et al. | |
| 5,778,820 A | 7/1998 | van der Lely et al. | |
| 6,007,548 A | 12/1999 | Ritchey | |
| 6,016,769 A | 1/2000 | Forster | |
| 6,043,748 A | 3/2000 | Touchton et al. | |
| 6,053,926 A | 4/2000 | Luehrs | |
| 6,095,915 A | 8/2000 | Geissler et al. | |
| 6,099,482 A | 8/2000 | Brune et al. | |
| 6,100,804 A | 8/2000 | Brady et al. | |
| 6,113,539 A | 9/2000 | Ridenour | |
| 6,114,957 A | 9/2000 | Westrick et al. | |
| 6,145,225 A | 11/2000 | Ritchey | |
| 6,166,643 A | 12/2000 | Janning et al. | |
| 6,172,640 B1 | 1/2001 | Durst et al. | |
| 6,232,880 B1 | 5/2001 | Anderson et al. | |
| 6,235,036 B1 | 5/2001 | Gardner et al. | |
| 6,271,757 B1 | 8/2001 | Touchton et al. | |
| 6,297,739 B1 | 10/2001 | Small | |
| 6,310,553 B1 | 10/2001 | Dance | |
| 6,402,692 B1 | 6/2002 | Morford | |
| 6,476,541 B1* | 11/2002 | Smith | G01N 29/348 310/334 |
| 6,497,197 B1 | 12/2002 | Huisma | |
| 6,502,060 B1 | 12/2002 | Christian | |
| 6,510,630 B1 | 1/2003 | Gardner | |
| 6,535,131 B1 | 3/2003 | Bar-Shalom et al. | |
| 6,569,092 B1 | 5/2003 | Guichon et al. | |
| 6,659,039 B1 | 12/2003 | Larsen | |
| 6,868,804 B1 | 3/2005 | Huisma et al. | |
| 7,016,730 B2 | 3/2006 | Ternes | |
| 7,046,152 B1 | 5/2006 | Peinetti et al. | |
| 7,137,359 B1 | 11/2006 | Braden | |
| 7,296,539 B2 | 11/2007 | Iljas | |
| 7,380,518 B2 | 6/2008 | Kates | |
| 7,705,736 B1 | 4/2010 | Kedziora | |
| 7,772,979 B2 | 8/2010 | Nehls | |
| 7,843,350 B2 | 11/2010 | Geissler et al. | |
| 7,937,861 B1 | 5/2011 | Zacher | |
| 8,005,624 B1 | 8/2011 | Starr | |
| 8,266,990 B1 | 9/2012 | Janson | |
| 8,305,220 B2 | 11/2012 | Gibson | |
| 8,478,389 B1 | 7/2013 | Brockway et al. | |
| 8,622,929 B2 | 1/2014 | Wilson et al. | |
| 8,763,557 B2 | 7/2014 | Lipscomb et al. | |
| 8,955,462 B1 | 2/2015 | Golden et al. | |
| 9,215,862 B2 | 12/2015 | Bladen et al. | |
| 9,392,767 B2 | 7/2016 | Talt et al. | |
| 9,392,946 B1 | 7/2016 | Sarantos et al. | |
| 9,449,487 B1 | 9/2016 | Spitalny | |
| 9,648,849 B1 | 5/2017 | Vivathana | |
| 9,654,925 B1 | 5/2017 | Solinsky et al. | |
| 9,693,536 B1 | 7/2017 | Dana | |
| 9,717,216 B1 | 8/2017 | Schlachta et al. | |
| 9,743,643 B1 | 8/2017 | Kaplan et al. | |
| 9,848,577 B1 | 12/2017 | Brandao et al. | |
| 9,861,080 B1 | 1/2018 | Hathway et al. | |
| 10,021,857 B2 | 7/2018 | Bailey et al. | |
| 10,039,263 B2 | 8/2018 | Teychene et al. | |
| 10,045,511 B1 | 8/2018 | Yarden et al. | |
| 10,064,391 B1 | 9/2018 | Riley | |
| 10,091,972 B1 | 10/2018 | Jensen et al. | |
| 10,231,442 B1 | 3/2019 | Chang et al. | |
| 10,242,547 B1 | 3/2019 | Struhsaker et al. | |
| 10,264,762 B1 | 4/2019 | Lamb | |
| 10,352,759 B1 | 7/2019 | Jensen | |
| 10,446,006 B1 | 10/2019 | Johnson, Jr. et al. | |
| 10,512,430 B1 | 12/2019 | Hladio | |
| 10,588,295 B1 | 3/2020 | Riley | |
| 10,628,756 B1 | 4/2020 | Kuper et al. | |
| 10,638,726 B1 | 5/2020 | Makarychev et al. | |
| 10,691,674 B2 | 6/2020 | Leong et al. | |
| 2001/0027751 A1 | 10/2001 | van den Berg | |
| 2002/0009015 A1* | 1/2002 | Lagharn, Jr. | B01J 19/10 366/108 |
| 2002/0010390 A1 | 1/2002 | Guice et al. | |
| 2002/0021219 A1 | 2/2002 | Edwards | |
| 2002/0091326 A1 | 7/2002 | Hashimoto et al. | |
| 2002/0095828 A1 | 7/2002 | Koopman et al. | |
| 2002/0154015 A1 | 10/2002 | Hixson | |
| 2002/0158765 A1 | 10/2002 | Pape et al. | |
| 2003/0004652 A1 | 1/2003 | Brunner et al. | |
| 2003/0023517 A1 | 1/2003 | Marsh et al. | |
| 2003/0024317 A1* | 2/2003 | Miller | G10K 11/002 73/626 |
| 2003/0062001 A1 | 4/2003 | Hakan | |
| 2003/0066491 A1 | 4/2003 | Stampe | |
| 2003/0144926 A1 | 7/2003 | Bodin et al. | |
| 2003/0146284 A1 | 8/2003 | Schmit et al. | |
| 2003/0149526 A1 | 8/2003 | Zhou et al. | |
| 2003/0177025 A1 | 9/2003 | Curkendall et al. | |
| 2003/0201931 A1 | 10/2003 | Durst et al. | |
| 2003/0208157 A1 | 11/2003 | Eidson et al. | |
| 2003/0221343 A1 | 12/2003 | Volk et al. | |

(56) References Cited

U.S. PATENT DOCUMENTS

| | | |
|---|---|---|
| 2003/0229452 A1 | 12/2003 | Lewis |
| 2004/0066298 A1 | 4/2004 | Schmitt et al. |
| 2004/0078390 A1 | 4/2004 | Saunders |
| 2004/0118920 A1 | 6/2004 | He |
| 2004/0123810 A1 | 7/2004 | Lorton et al. |
| 2004/0177011 A1 | 9/2004 | Ramsay et al. |
| 2004/0201454 A1 | 10/2004 | Waterhouse et al. |
| 2005/0000279 A1 | 1/2005 | Yogeswaren |
| 2005/0010333 A1 | 1/2005 | Lorton et al. |
| 2005/0026181 A1 | 2/2005 | Davis et al. |
| 2005/0097997 A1 | 5/2005 | Hile |
| 2005/0108912 A1 | 5/2005 | Bekker |
| 2005/0115508 A1 | 6/2005 | Little |
| 2005/0128086 A1 | 6/2005 | Brown et al. |
| 2005/0139168 A1 | 6/2005 | Light et al. |
| 2005/0145187 A1 | 7/2005 | Gray |
| 2005/0273117 A1 | 12/2005 | Teychene |
| 2005/0279287 A1 | 12/2005 | Kroeker |
| 2005/0284381 A1 | 12/2005 | Bell et al. |
| 2006/0011145 A1 | 1/2006 | Kates |
| 2006/0052986 A1 | 3/2006 | Rogers et al. |
| 2006/0064325 A1 | 3/2006 | Suzuken |
| 2006/0087440 A1 | 4/2006 | Klein |
| 2006/0106289 A1 | 5/2006 | Elser |
| 2006/0117619 A1 | 6/2006 | Costantini |
| 2006/0155172 A1 | 7/2006 | Rugg |
| 2006/0170561 A1 | 8/2006 | Eyal |
| 2006/0173367 A1 | 8/2006 | Stuart et al. |
| 2006/0185605 A1 | 8/2006 | Renz et al. |
| 2006/0201436 A1 | 9/2006 | Kates |
| 2006/0207515 A1 | 9/2006 | Palett |
| 2006/0241521 A1 | 10/2006 | Cohen |
| 2006/0282274 A1 | 12/2006 | Bennett |
| 2006/0290514 A1 | 12/2006 | Sakama et al. |
| 2007/0006494 A1 | 1/2007 | Hayes et al. |
| 2007/0008155 A1 | 1/2007 | Trost et al. |
| 2007/0021660 A1 | 1/2007 | Delonzor et al. |
| 2007/0027375 A1 | 2/2007 | Melker et al. |
| 2007/0027377 A1 | 2/2007 | Delonzor et al. |
| 2007/0027379 A1 | 2/2007 | Delonzor et al. |
| 2007/0029381 A1 | 2/2007 | Braiman |
| 2007/0044317 A1 | 3/2007 | Critelli |
| 2007/0044732 A1 | 3/2007 | Araki et al. |
| 2007/0062457 A1 | 3/2007 | Bates et al. |
| 2007/0069899 A1 | 3/2007 | Shih et al. |
| 2007/0103296 A1 | 5/2007 | Paessel et al. |
| 2007/0149871 A1 | 6/2007 | Sarussi et al. |
| 2007/0152825 A1 | 7/2007 | August et al. |
| 2007/0222624 A1 | 9/2007 | Eicken et al. |
| 2007/0255124 A1 | 11/2007 | Pologe et al. |
| 2007/0258625 A1 | 11/2007 | Mirtsching |
| 2007/0283791 A1 | 12/2007 | Engvall et al. |
| 2007/0298421 A1 | 12/2007 | Jiang et al. |
| 2008/0001815 A1 | 1/2008 | Wang et al. |
| 2008/0004798 A1 | 1/2008 | Troxler et al. |
| 2008/0017126 A1 | 1/2008 | Adams et al. |
| 2008/0018481 A1 | 1/2008 | Zehavi |
| 2008/0021352 A1 | 1/2008 | Keegan et al. |
| 2008/0036610 A1 | 2/2008 | Hokuf et al. |
| 2008/0047177 A1 | 2/2008 | Hilpert |
| 2008/0055155 A1 | 3/2008 | Hensley et al. |
| 2008/0059263 A1 | 3/2008 | Stroman et al. |
| 2008/0061990 A1 | 3/2008 | Mines et al. |
| 2008/0076988 A1 | 3/2008 | Sarussi et al. |
| 2008/0076992 A1 | 3/2008 | Hete et al. |
| 2008/0085522 A1 | 4/2008 | Meghen et al. |
| 2008/0097726 A1 | 4/2008 | Lorton et al. |
| 2008/0110406 A1 | 5/2008 | Anderson et al. |
| 2008/0125658 A1 | 5/2008 | Lee et al. |
| 2008/0146890 A1 | 6/2008 | LeBoeuf et al. |
| 2008/0173255 A1 | 7/2008 | Mainini et al. |
| 2008/0190202 A1 | 8/2008 | Kulach et al. |
| 2008/0190379 A1 | 8/2008 | Mainini et al. |
| 2008/0215484 A1 | 9/2008 | Oldham |
| 2008/0227662 A1 | 9/2008 | Stromberg et al. |
| 2008/0228105 A1 | 9/2008 | Howell et al. |
| 2008/0262326 A1 | 10/2008 | Hete et al. |
| 2008/0272908 A1 | 11/2008 | Boyd |
| 2008/0312511 A1 | 12/2008 | Osler et al. |
| 2009/0009388 A1 | 1/2009 | Wangrud |
| 2009/0020613 A1 | 1/2009 | Chang et al. |
| 2009/0025651 A1 | 1/2009 | Lalor |
| 2009/0058730 A1 | 3/2009 | Geissler et al. |
| 2009/0094869 A1 | 4/2009 | Geissler et al. |
| 2009/0102668 A1 | 4/2009 | Thompson et al. |
| 2009/0139462 A1 | 6/2009 | So |
| 2009/0149727 A1 | 6/2009 | Truitt et al. |
| 2009/0187392 A1 | 7/2009 | Riskey et al. |
| 2009/0255484 A1 | 10/2009 | Muelken |
| 2009/0312667 A1 | 12/2009 | Utsunomiya et al. |
| 2010/0018363 A1 | 1/2010 | Chervenak et al. |
| 2010/0030036 A1 | 2/2010 | Mottram et al. |
| 2010/0045468 A1 | 2/2010 | Geissler |
| 2010/0113902 A1 | 5/2010 | Hete et al. |
| 2010/0139575 A1 | 6/2010 | Duncan et al. |
| 2010/0160809 A1 | 6/2010 | Laurence et al. |
| 2010/0175625 A1 | 7/2010 | Klenotiz |
| 2010/0217102 A1 | 8/2010 | LeBoeuf et al. |
| 2010/0250198 A1 | 9/2010 | Lorton et al. |
| 2010/0289639 A1 | 11/2010 | Gibson et al. |
| 2010/0315241 A1 | 12/2010 | Jow |
| 2010/0317972 A1 | 12/2010 | Baumgartner et al. |
| 2010/0321182 A1 | 12/2010 | Wangrud |
| 2010/0321189 A1 | 12/2010 | Gibson et al. |
| 2010/0331739 A1 | 12/2010 | Afikim et al. |
| 2011/0018717 A1 | 1/2011 | Takahashi et al. |
| 2011/0041367 A1 | 2/2011 | Bladen et al. |
| 2011/0061605 A1 | 3/2011 | Hardi et al. |
| 2011/0095089 A1 | 4/2011 | Kolton et al. |
| 2011/0121356 A1 | 5/2011 | Krawinkel et al. |
| 2011/0137185 A1 | 6/2011 | Hete et al. |
| 2011/0152876 A1 | 6/2011 | Vandeputte |
| 2011/0178423 A1 | 7/2011 | Hatch |
| 2011/0203144 A1 | 8/2011 | Junek et al. |
| 2011/0258130 A1 | 10/2011 | Grabiner et al. |
| 2011/0272470 A1 | 11/2011 | Baba et al. |
| 2011/0313264 A1 | 12/2011 | Hete |
| 2012/0009943 A1 | 1/2012 | Greenberg et al. |
| 2012/0068848 A1 | 3/2012 | Campbell et al. |
| 2012/0089152 A1 | 4/2012 | Lynd et al. |
| 2012/0092132 A1 | 4/2012 | Holme et al. |
| 2012/0111286 A1 | 5/2012 | Lee et al. |
| 2012/0112917 A1 | 5/2012 | Menachem et al. |
| 2012/0160181 A1 | 6/2012 | So et al. |
| 2012/0175412 A1 | 7/2012 | Grabiner et al. |
| 2012/0204811 A1 | 8/2012 | Ryan |
| 2012/0236690 A1 | 9/2012 | Rader et al. |
| 2012/0291715 A1 | 11/2012 | Jiang et al. |
| 2012/0299731 A1 | 11/2012 | Triener |
| 2012/0320710 A1 | 12/2012 | Sato et al. |
| 2012/0326862 A1 | 12/2012 | Kwak et al. |
| 2012/0326874 A1 | 12/2012 | Kwak et al. |
| 2013/0006065 A1 | 1/2013 | Yanai et al. |
| 2013/0014706 A1 | 1/2013 | Menkes |
| 2013/0046170 A1 | 2/2013 | Haynes |
| 2013/0113622 A1 | 5/2013 | Pratt et al. |
| 2013/0119142 A1 | 5/2013 | McCoy et al. |
| 2013/0175347 A1 | 7/2013 | Decaluwe et al. |
| 2013/0192526 A1 | 8/2013 | Mainini |
| 2013/0211773 A1 | 8/2013 | Loeschinger et al. |
| 2013/0222141 A1 | 8/2013 | Rhee et al. |
| 2013/0237778 A1 | 9/2013 | Rouquette et al. |
| 2013/0239904 A1 | 9/2013 | Kim et al. |
| 2013/0239907 A1 | 9/2013 | Laurence et al. |
| 2013/0241356 A1 | 9/2013 | Kim et al. |
| 2013/0265165 A1 | 10/2013 | So et al. |
| 2013/0285815 A1 | 10/2013 | Jones, II |
| 2014/0062259 A1 | 3/2014 | Lautzenhiser et al. |
| 2014/0073486 A1 | 3/2014 | Ahmed et al. |
| 2014/0122488 A1 | 5/2014 | Jung et al. |
| 2014/0123912 A1 | 5/2014 | Menkes et al. |
| 2014/0135596 A1 | 5/2014 | LeBoeuf et al. |
| 2014/0135631 A1 | 5/2014 | Brumback et al. |
| 2014/0171762 A1 | 6/2014 | LeBoeuf et al. |

(56) References Cited

U.S. PATENT DOCUMENTS

| | | |
|---|---|---|
| 2014/0174376 A1 | 6/2014 | Touchton et al. |
| 2014/0196673 A1 | 7/2014 | Menkes et al. |
| 2014/0230755 A1 | 8/2014 | Trenkle et al. |
| 2014/0232541 A1 | 8/2014 | Trenkle et al. |
| 2014/0253709 A1 | 9/2014 | Bresch et al. |
| 2014/0254325 A1 | 9/2014 | Korbler et al. |
| 2014/0261235 A1 | 9/2014 | Rich et al. |
| 2014/0267299 A1 | 9/2014 | Couse |
| 2014/0275824 A1 | 9/2014 | Couse |
| 2014/0276089 A1 | 9/2014 | Kirenko et al. |
| 2014/0290013 A1 | 10/2014 | Eidelman et al. |
| 2014/0302783 A1 | 10/2014 | Aiuto et al. |
| 2014/0331942 A1 | 11/2014 | Sarazyn |
| 2014/0333439 A1 | 11/2014 | Downing et al. |
| 2014/0347184 A1 | 11/2014 | Triener |
| 2014/0352632 A1 | 12/2014 | McLaughlin |
| 2014/0368338 A1 | 12/2014 | Rettedal et al. |
| 2015/0025394 A1 | 1/2015 | Hong et al. |
| 2015/0039239 A1 | 2/2015 | Shuler et al. |
| 2015/0057963 A1 | 2/2015 | Zakharov et al. |
| 2015/0097668 A1 | 4/2015 | Toth |
| 2015/0099472 A1 | 4/2015 | Ickovic |
| 2015/0100245 A1 | 4/2015 | Huang et al. |
| 2015/0107519 A1 | 4/2015 | Rajkondawar et al. |
| 2015/0107522 A1 | 4/2015 | Lamb |
| 2015/0122893 A1 | 5/2015 | Warther |
| 2015/0128873 A1 | 5/2015 | Prescott et al. |
| 2015/0130617 A1 | 5/2015 | Triener |
| 2015/0148811 A1 | 5/2015 | Swope et al. |
| 2015/0157435 A1 | 6/2015 | Chasins et al. |
| 2015/0182322 A1 | 7/2015 | Couse et al. |
| 2015/0245592 A1 | 9/2015 | Sibbald et al. |
| 2015/0282457 A1 | 10/2015 | Yarden |
| 2015/0334994 A1 | 11/2015 | Prasad |
| 2015/0342143 A1 | 12/2015 | Stewart |
| 2015/0351885 A1 | 12/2015 | Kool et al. |
| 2015/0366166 A1 | 12/2015 | Mueller |
| 2016/0000045 A1 | 1/2016 | Funaya et al. |
| 2016/0021506 A1 | 1/2016 | Bonge, Jr. |
| 2016/0058379 A1 | 3/2016 | Menkes et al. |
| 2016/0066546 A1 | 3/2016 | Borchersen et al. |
| 2016/0100802 A1 | 4/2016 | Newman |
| 2016/0106064 A1 | 4/2016 | Bladen et al. |
| 2016/0113524 A1 | 4/2016 | Gross et al. |
| 2016/0120154 A1 | 5/2016 | Hill et al. |
| 2016/0128637 A1 | 5/2016 | LeBoeuf et al. |
| 2016/0135431 A1 | 5/2016 | Siegel |
| 2016/0148086 A1 | 5/2016 | Clarke et al. |
| 2016/0150362 A1 | 5/2016 | Shaprio et al. |
| 2016/0151013 A1 | 6/2016 | Atallah et al. |
| 2016/0165851 A1 | 6/2016 | Harty et al. |
| 2016/0165852 A1 | 6/2016 | Goldfain |
| 2016/0166761 A1 | 6/2016 | Piehl et al. |
| 2016/0198957 A1 | 7/2016 | Arditi et al. |
| 2016/0210841 A1 | 7/2016 | Huang |
| 2016/0213317 A1 | 7/2016 | Richardson et al. |
| 2016/0278712 A1 | 9/2016 | Sagara et al. |
| 2016/0286757 A1 | 10/2016 | Armstrong |
| 2016/0287108 A1 | 10/2016 | Wei et al. |
| 2016/0317049 A1 | 11/2016 | LeBoeuf et al. |
| 2016/0345881 A1 | 12/2016 | Sarantos et al. |
| 2016/0360733 A1 | 12/2016 | Triener |
| 2016/0367495 A1 | 12/2016 | Miller et al. |
| 2017/0000090 A1 | 1/2017 | Hall |
| 2017/0006836 A1 | 1/2017 | Torres |
| 2017/0042119 A1 | 2/2017 | Garrity |
| 2017/0067770 A1 | 3/2017 | Sun |
| 2017/0079247 A1 | 3/2017 | Womble et al. |
| 2017/0095206 A1 | 4/2017 | Leib et al. |
| 2017/0156288 A1 | 6/2017 | Singh |
| 2017/0164905 A1 | 6/2017 | Gumiero |
| 2017/0193208 A1 | 7/2017 | Ashley et al. |
| 2017/0196203 A1 | 7/2017 | Huisma et al. |
| 2017/0202185 A1 | 7/2017 | Trumbull et al. |
| 2017/0245797 A1 | 8/2017 | Quinn |
| 2017/0258039 A1 | 9/2017 | Lauterbach |
| 2017/0272842 A1 | 9/2017 | Touma |
| 2017/0280675 A1 | 10/2017 | MacNeil et al. |
| 2017/0280688 A1 | 10/2017 | Deliou et al. |
| 2017/0318781 A1 | 11/2017 | Rollins et al. |
| 2017/0360004 A1 | 12/2017 | Carver |
| 2017/0372583 A1 | 12/2017 | Lamkin et al. |
| 2018/0000045 A1 | 1/2018 | Bianchi et al. |
| 2018/0007863 A1 | 1/2018 | Bailey et al. |
| 2018/0014512 A1 | 1/2018 | Arabani et al. |
| 2018/0055016 A1 | 3/2018 | Hsieh et al. |
| 2018/0064068 A1 | 3/2018 | McKee et al. |
| 2018/0070559 A1 | 3/2018 | So |
| 2018/0098522 A1 | 4/2018 | Steinfort |
| 2018/0110205 A1 | 4/2018 | Czarnecky et al. |
| 2018/0131074 A1 | 5/2018 | Wilkinson et al. |
| 2018/0132455 A1 | 5/2018 | Pradeep et al. |
| 2018/0206455 A1 | 7/2018 | Thiex et al. |
| 2018/0242860 A1 | 8/2018 | LeBoeuf et al. |
| 2018/0249683 A1 | 9/2018 | Borchersen et al. |
| 2018/0260976 A1 | 9/2018 | Watanabe et al. |
| 2018/0271058 A1 | 9/2018 | Valdez |
| 2018/0279582 A1 | 10/2018 | Yajima et al. |
| 2018/0288968 A1 | 10/2018 | Cisco |
| 2018/0295809 A1 | 10/2018 | Yajima et al. |
| 2018/0303425 A1 | 10/2018 | Wordham et al. |
| 2018/0310526 A1 | 11/2018 | Birch et al. |
| 2018/0325382 A1 | 11/2018 | Brandao et al. |
| 2018/0332989 A1 | 11/2018 | Chiu et al. |
| 2018/0333244 A1 | 11/2018 | Hanks et al. |
| 2019/0008118 A1 | 1/2019 | Keegan |
| 2019/0008124 A1 | 1/2019 | Komatsu et al. |
| 2019/0029226 A1 | 1/2019 | Triener |
| 2019/0053469 A1 | 2/2019 | Mardirossian |
| 2019/0053470 A1 | 2/2019 | Singh et al. |
| 2019/0059335 A1 | 2/2019 | Crider, Jr. et al. |
| 2019/0059337 A1 | 2/2019 | Robbins |
| 2019/0059741 A1 | 2/2019 | Crider, Jr. et al. |
| 2019/0069512 A1 | 3/2019 | Eriksson et al. |
| 2019/0075945 A1 | 3/2019 | Strassburger et al. |
| 2019/0082654 A1 | 3/2019 | Robbins |
| 2019/0090754 A1 | 3/2019 | Brandao et al. |
| 2019/0110433 A1 | 4/2019 | Myers |
| 2019/0110436 A1 | 4/2019 | Gardner et al. |
| 2019/0125509 A1 | 5/2019 | Hotchkin |
| 2019/0130728 A1 | 5/2019 | Struhsaker et al. |
| 2019/0133086 A1 | 5/2019 | Katz et al. |
| 2019/0159428 A1 | 5/2019 | Bolen |
| 2019/0166802 A1 | 6/2019 | Seltzer et al. |
| 2019/0183091 A1 | 6/2019 | Betts-LaCroix et al. |
| 2019/0183092 A1 | 6/2019 | Couse et al. |
| 2019/0208358 A1 | 7/2019 | de Barros Chapiewski et al. |
| 2019/0213860 A1 | 7/2019 | Shaprio et al. |
| 2019/0254599 A1 | 8/2019 | Young et al. |
| 2019/0287429 A1 | 9/2019 | Dawson et al. |
| 2019/0290133 A1 | 9/2019 | Crider et al. |
| 2019/0290847 A1 | 9/2019 | Veyrent et al. |
| 2019/0298226 A1 | 10/2019 | Filipowicz |
| 2019/0298924 A1 | 10/2019 | Gibson et al. |
| 2019/0302063 A1* | 10/2019 | Hadimioglu ............ G01N 29/28 |
| 2019/0327939 A1 | 10/2019 | Sharpe et al. |
| 2019/0335715 A1 | 11/2019 | Hicks et al. |
| 2019/0350168 A1 | 11/2019 | Shi |
| 2019/0365324 A1 | 12/2019 | Chang |
| 2019/0373857 A1 | 12/2019 | Leigh-Lancaster et al. |
| 2019/0380311 A1 | 12/2019 | Crouthamel et al. |
| 2019/0385037 A1 | 12/2019 | Robadey et al. |
| 2019/0385332 A1 | 12/2019 | Yajima et al. |
| 2020/0015740 A1 | 1/2020 | Alnofeli et al. |
| 2020/0037886 A1 | 2/2020 | Greer et al. |
| 2020/0068853 A1 | 3/2020 | Radovcic |
| 2020/0085019 A1 | 3/2020 | Gilbert et al. |
| 2020/0100463 A1 | 4/2020 | Rooda et al. |
| 2020/0107522 A1 | 4/2020 | Kersey et al. |
| 2020/0110946 A1 | 4/2020 | Kline et al. |
| 2020/0113728 A1 | 4/2020 | Spector et al. |
| 2020/0170222 A1 | 6/2020 | Gotts |
| 2020/0178505 A1 | 6/2020 | Womble et al. |
| 2020/0178800 A1 | 6/2020 | Geissler et al. |

(56) References Cited

U.S. PATENT DOCUMENTS

| | | | |
|---|---|---|---|
| 2020/0205381 A1 | 7/2020 | Wernimont et al. | |
| 2020/0229391 A1 | 7/2020 | De Groot | |
| 2020/0229707 A1 | 7/2020 | Donnelly | |
| 2020/0242551 A1 | 7/2020 | Lau et al. | |

FOREIGN PATENT DOCUMENTS

| | | |
|---|---|---|
| AU | 2003238759 | 1/2004 |
| AU | 2004263067 | 2/2005 |
| AU | 2004305403 | 7/2005 |
| AU | 2011210083 | 8/2011 |
| AU | 2016266101 | 12/2016 |
| AU | 2017100469 | 5/2017 |
| AU | 2018220079 | 9/2018 |
| BR | 11201201890 9 | 1/2011 |
| CA | 2267812 | 10/2000 |
| CA | 2493331 | 1/2005 |
| CA | 2788153 | 8/2011 |
| CA | 2880138 | 2/2013 |
| CA | 2858905 | 10/2013 |
| CA | 2875637 | 1/2014 |
| CA | 2875578 | 12/2014 |
| CA | 2915843 | 12/2014 |
| CA | 2990620 | 12/2016 |
| CA | 2916286 | 6/2017 |
| CA | 3007296 | 6/2017 |
| CN | 1989895 | 7/2007 |
| CN | 201171316 | 12/2008 |
| CN | 101578516 | 11/2009 |
| CN | 101816290 | 9/2010 |
| CN | 101875975 | 11/2010 |
| CN | 101875976 | 11/2010 |
| CN | 102781225 | 1/2011 |
| CN | 102142116 | 8/2011 |
| CN | 102485892 | 6/2012 |
| CN | 102682322 | 9/2012 |
| CN | 103300893 A | 9/2013 |
| CN | 203313865 | 12/2013 |
| CN | 203689049 | 2/2014 |
| CN | 203523519 | 4/2014 |
| CN | 204047531 | 8/2014 |
| CN | 204305813 | 5/2015 |
| CN | 204331349 | 5/2015 |
| CN | 105080822 A | 11/2015 |
| CN | 105191817 | 12/2015 |
| CN | 106125648 | 11/2016 |
| CN | 106172068 | 12/2016 |
| CN | 106197675 | 12/2016 |
| CN | 106719037 | 2/2017 |
| CN | 205919898 | 2/2017 |
| CN | 106472347 | 3/2017 |
| CN | 106845598 | 6/2017 |
| CN | 206431665 | 8/2017 |
| CN | 107201409 | 9/2017 |
| CN | 207201674 | 9/2017 |
| CN | 107251851 | 10/2017 |
| CN | 107667898 | 2/2018 |
| CN | 108353810 | 2/2018 |
| CN | 207100094 | 3/2018 |
| CN | 207249710 | 4/2018 |
| CN | 108651301 | 5/2018 |
| CN | 108656996 | 5/2018 |
| CN | 108684549 | 5/2018 |
| CN | 108118096 | 6/2018 |
| CN | 108308055 | 7/2018 |
| CN | 109006541 | 8/2018 |
| CN | 109008529 | 8/2018 |
| CN | 108617533 | 10/2018 |
| CN | 108717668 | 10/2018 |
| CN | 108766586 | 11/2018 |
| CN | 109006550 | 12/2018 |
| CN | 208273869 | 12/2018 |
| CN | 109355402 | 2/2019 |
| CN | 109937904 | 3/2019 |
| CN | 109937905 | 3/2019 |
| CN | 109823691 | 5/2019 |
| CN | 110073995 | 5/2019 |
| CN | 110059781 | 7/2019 |
| CN | 110106261 | 8/2019 |
| CN | 110106262 | 8/2019 |
| CN | 110506656 | 11/2019 |
| CN | 210076292 | 2/2020 |
| DE | 633742 | 8/1936 |
| DE | 2850438 | 5/1980 |
| DE | 19629166 | 2/1997 |
| DE | 19826348 | 6/1998 |
| DE | 29906146 | 6/1999 |
| DE | 19911766 | 9/2000 |
| DE | 20018364 | 1/2001 |
| DE | 10001176 | 5/2001 |
| DE | 102004027978 | 12/2005 |
| DE | 202010008325 | 2/2012 |
| DE | 202016101289 | 4/2016 |
| DK | 140001 | 11/1979 |
| EP | 55127 | 6/1982 |
| EP | 125915 | 11/1984 |
| EP | 0499428 | 8/1992 |
| EP | 513525 | 11/1992 |
| EP | 743043 | 11/1996 |
| EP | 938841 | 2/1998 |
| EP | 898449 | 3/1999 |
| EP | 1076485 | 2/2001 |
| EP | 1445723 | 8/2004 |
| EP | 1479338 | 11/2004 |
| EP | 1521208 | 4/2005 |
| EP | 1907816 | 4/2008 |
| EP | 1961294 | 8/2008 |
| EP | 2028931 | 3/2009 |
| EP | 2172878 | 4/2010 |
| EP | 2453733 | 5/2012 |
| EP | 2465344 | 6/2012 |
| EP | 2488237 | 8/2012 |
| EP | 2528431 | 12/2012 |
| EP | 2534945 | 12/2012 |
| EP | 2657889 | 10/2013 |
| EP | 2664234 | 11/2013 |
| EP | 2728995 | 5/2014 |
| EP | 2879615 | 6/2015 |
| EP | 2955998 | 12/2015 |
| EP | 3153098 | 4/2017 |
| EP | 3164855 | 5/2017 |
| EP | 3210531 | 8/2017 |
| EP | 3217566 | 9/2017 |
| EP | 3218865 | 9/2017 |
| EP | 3225106 | 10/2017 |
| EP | 3316680 | 5/2018 |
| EP | 3346422 | 7/2018 |
| EP | 3385886 | 10/2018 |
| EP | 3593634 | 1/2020 |
| EP | 3627856 | 3/2020 |
| EP | 3660855 | 6/2020 |
| ES | 2046912 | 2/1994 |
| ES | 2206009 | 5/2004 |
| ES | 2215152 | 10/2004 |
| ES | 2239500 A1 | 9/2005 |
| ES | 1072416 | 7/2010 |
| ES | 2391341 | 11/2012 |
| ES | 1194609 | 10/2017 |
| FI | 20165318 | 6/2017 |
| FR | 2106705 | 5/1972 |
| FR | 2297565 | 8/1976 |
| FR | 2342024 | 1/1983 |
| FR | 2601848 | 1/1988 |
| FR | 2779153 | 12/1999 |
| FR | 2834521 | 7/2003 |
| FR | 2964777 | 3/2012 |
| FR | 3046332 | 1/2016 |
| FR | 3024653 | 2/2016 |
| FR | 3085249 | 9/2018 |
| GB | 588870 | 6/1947 |
| GB | 641394 | 8/1950 |
| GB | 865164 | 4/1961 |
| GB | 1072971 | 6/1967 |
| GB | 1267830 | 3/1972 |

(56) References Cited

FOREIGN PATENT DOCUMENTS

| | | |
|---|---|---|
| GB | 1415650 | 11/1975 |
| GB | 2067121 | 7/1981 |
| GB | 2055670 | 7/1983 |
| GB | 2114045 | 8/1983 |
| GB | 2125343 | 3/1984 |
| GB | 2142812 | 1/1985 |
| GB | 2392138 | 2/2004 |
| GB | 2469326 | 10/2010 |
| GB | 2554636 | 9/2016 |
| GB | 2570340 | 7/2019 |
| GB | 2571404 | 8/2019 |
| IN | 201103443 | 12/2011 |
| IN | 200802272 | 6/2016 |
| JP | 57173562 | 11/1982 |
| JP | 7177832 | 7/1995 |
| JP | 2001178692 | 7/2001 |
| JP | 2004292151 | 10/2004 |
| JP | 2005102959 | 4/2005 |
| JP | 5659243 | 1/2011 |
| JP | 2011067178 | 4/2011 |
| JP | 2011087657 | 5/2011 |
| JP | 2013247941 | 6/2012 |
| JP | 2016225891 A | 12/2016 |
| JP | 2017112857 | 6/2017 |
| JP | 2017002170 | 4/2018 |
| KR | 2003061157 | 7/2003 |
| KR | 2005046330 | 5/2005 |
| KR | 780449 | 11/2007 |
| KR | 101747418 | 1/2011 |
| KR | 20130019970 | 2/2013 |
| KR | 20130057683 | 6/2013 |
| KR | 2013138899 | 12/2013 |
| KR | 2019061805 | 11/2017 |
| KR | 101827311 | 2/2018 |
| KR | 20180035537 | 4/2018 |
| KR | 2018109451 | 10/2018 |
| KR | 20190081598 | 7/2019 |
| KR | 2019091708 | 8/2019 |
| MX | 9600754 | 2/1997 |
| MX | 356331 | 1/2011 |
| NL | 2017104 | 1/2018 |
| NL | 2019186 | 1/2019 |
| NL | 2020275 | 7/2019 |
| NZ | 198486 | 5/1986 |
| NZ | 199494 | 7/1986 |
| NZ | 203924 | 10/1986 |
| NZ | 335702 | 3/2001 |
| NZ | 507129 | 8/2002 |
| NZ | 582984 | 1/2011 |
| RU | 2178711 | 1/2002 |
| RU | 2265324 | 12/2005 |
| SE | 4567 | 3/1893 |
| SE | 5549 | 4/1894 |
| SE | 123213 | 11/1948 |
| SE | 188102 | 3/1964 |
| SU | 1766336 | 10/1992 |
| WO | 1984000468 | 2/1984 |
| WO | 1991011956 | 8/1991 |
| WO | 199302549 | 2/1993 |
| WO | 199822028 | 5/1998 |
| WO | 1998039475 | 9/1998 |
| WO | 1999017658 | 4/1999 |
| WO | 2000062263 | 4/1999 |
| WO | 9945761 | 9/1999 |
| WO | 2000013393 | 3/2000 |
| WO | 2000061802 | 10/2000 |
| WO | 2001004969 A1 | 1/2001 |
| WO | 2001033950 | 5/2001 |
| WO | 2001087054 | 11/2001 |
| WO | 2002031629 | 4/2002 |
| WO | 2002085106 | 10/2002 |
| WO | 2003001180 | 1/2003 |
| WO | 2004092920 | 3/2003 |
| WO | 2003087765 | 10/2003 |
| WO | 2003094605 | 11/2003 |
| WO | 2004015655 | 2/2004 |
| WO | 2005104775 | 4/2004 |
| WO | 2006078943 | 1/2005 |
| WO | 2005104930 | 4/2005 |
| WO | 2005073408 | 8/2005 |
| WO | 2005082132 A2 | 9/2005 |
| WO | 2006021855 | 3/2006 |
| WO | 2006134197 | 12/2006 |
| WO | 2006135265 | 12/2006 |
| WO | 2007034211 | 3/2007 |
| WO | 2007095684 | 8/2007 |
| WO | 2007122375 | 11/2007 |
| WO | 2008033042 | 3/2008 |
| WO | 2008041839 A1 | 4/2008 |
| WO | 2008052298 | 5/2008 |
| WO | 2008075974 | 6/2008 |
| WO | 2010091686 | 12/2008 |
| WO | 2009034497 | 3/2009 |
| WO | 2009062249 | 5/2009 |
| WO | 2009076325 | 6/2009 |
| WO | 2009089215 | 7/2009 |
| WO | 2009117764 | 10/2009 |
| WO | 2009153779 | 12/2009 |
| WO | 2010008620 | 1/2010 |
| WO | 2010048753 | 5/2010 |
| WO | 2010053811 | 5/2010 |
| WO | 2010068713 | 6/2010 |
| WO | 2010140900 | 12/2010 |
| WO | 2012075480 | 12/2010 |
| WO | 2011039112 | 4/2011 |
| WO | 2011076886 | 6/2011 |
| WO | 2011154949 | 12/2011 |
| WO | 2012071670 | 6/2012 |
| WO | 2013008115 | 1/2013 |
| WO | 2013038326 | 3/2013 |
| WO | 2013082227 | 6/2013 |
| WO | 2015001537 | 7/2013 |
| WO | 2013118121 | 8/2013 |
| WO | 2015024050 | 8/2013 |
| WO | 2013179020 | 12/2013 |
| WO | 2013190423 | 12/2013 |
| WO | 2014020463 | 2/2014 |
| WO | 2014095759 | 6/2014 |
| WO | 2014107766 | 7/2014 |
| WO | 2014118788 | 8/2014 |
| WO | 2014125250 | 8/2014 |
| WO | 2016027271 | 8/2014 |
| WO | 2014140148 | 9/2014 |
| WO | 2014141084 | 9/2014 |
| WO | 2014194383 | 12/2014 |
| WO | 2014197631 | 12/2014 |
| WO | 2014199363 | 12/2014 |
| WO | 2015009167 | 1/2015 |
| WO | 2015030832 | 3/2015 |
| WO | 2015055709 | 4/2015 |
| WO | 2015086338 | 6/2015 |
| WO | 2016207844 | 6/2015 |
| WO | 2015107354 | 7/2015 |
| WO | 2017001717 | 7/2015 |
| WO | 2017031532 | 8/2015 |
| WO | 2015140486 | 9/2015 |
| WO | 2015142764 A1 | 9/2015 |
| WO | 2015158787 | 10/2015 |
| WO | 2015175686 | 11/2015 |
| WO | 2015176027 | 11/2015 |
| WO | 2015197385 | 12/2015 |
| WO | 2016037190 | 3/2016 |
| WO | 2017149049 | 3/2016 |
| WO | 2016053104 | 4/2016 |
| WO | 2016108187 | 7/2016 |
| WO | 2016166748 | 10/2016 |
| WO | 2017001538 | 1/2017 |
| WO | 2017027551 | 2/2017 |
| WO | 2017037479 | 3/2017 |
| WO | 2017066813 | 4/2017 |
| WO | 2017089289 | 6/2017 |
| WO | 2017096256 | 6/2017 |
| WO | 2017121834 | 7/2017 |
| WO | 2018006965 | 1/2018 |

(56) References Cited

FOREIGN PATENT DOCUMENTS

| WO | 2018011736 | | 1/2018 |
|---|---|---|---|
| WO | 2018019742 | | 2/2018 |
| WO | 2020022543 | | 7/2018 |
| WO | 2018172976 | | 9/2018 |
| WO | 2020060248 | | 9/2018 |
| WO | 2018203203 | | 11/2018 |
| WO | 2019009717 | | 1/2019 |
| WO | 2019025138 | | 2/2019 |
| WO | 2019046216 | | 3/2019 |
| WO | 2019048521 | A1 | 3/2019 |
| WO | 2019058752 | | 3/2019 |
| WO | 2019071222 | | 4/2019 |
| WO | 2019132803 | | 7/2019 |
| WO | 2019207561 | | 10/2019 |
| WO | 2019235942 | | 12/2019 |
| WO | 2019245978 | | 12/2019 |
| WO | 2020003310 | | 1/2020 |
| WO | 2020096528 | | 5/2020 |
| WO | 2020140013 | | 7/2020 |

OTHER PUBLICATIONS

Steensels, Machteld; Maltz, Ephraim; Bahr, Claudia; Berckmans, Daniel; Antler, Aharon; et al., Towards practical application of sensors for monitoring animal health: The effect of post-calving health problems on rumination duration, activity and milk yield, The Journal of Dairy Research; Cambridge vol. 84, Iss. 2, (May 2017): 132-138.

Clark, C., Lyons, N., Millapan, L., Talukder, S., Cronin, G., Kerrisk, K., Garcia, S. (2015), Rumination and activity levels as predictors of calving for dairy cows, Animal, 9(4), 691-695.

Koyama, T. Koyama, M. Sugimoto, N. Kusakari, R. Miura, K. Yoshioka, M. Hirako, Prediction of calving time in Holstein dairy cows by monitoring the ventral tail base surface temperature, The Veterinary Journal, vol. 240, 2018, pp. 1-5, ISSN 1090-0233.

L. Calamari, N. Soriani, G. Panella, F. Petrera, A. Minuti, E. Trevisi, Rumination time around calving: An early signal to detect cows at greater risk of disease, Journal of Dairy Science, vol. 97, Issue 6, 2014, pp. 3635-3647, ISSN 0022-0302.

S. Benaissa, F.A.M. Tuyttens, D. Plets, J. Trogh, L. Martens, L. Vandaele, W. Joseph, B. Sonck, Calving and estrus detection in dairy cattle using a combination of indoor localization and accelerometer sensors, Computers and Electronics in Agriculture, vol. 168, 2020, 105153, ISSN 0168-1699.

N. Soriani, E. Trevisi, L. Calamari, Relationships between rumination time, metabolic conditions, and health status in dairy Cows during the transition period, Journal of Animal Science, vol. 90, Issue 12, Dec. 2012, pp. 4544-4554.

The role of sensors, big data and machine learning in modern animal farming; Suresh Neethirajan; Accepted Jul. 3, 2020 Sensing and Bio-Sensing Research 29 (2020) 100367 2214-1804/ © 2020 the Author. Published by Elsevier B.V.

A Review on Determination of Computer Aid Diagnosis and/or Risk Factors Using Data Mining Methods in Veterinary Field Pinar Cihan, Erhan Gökçe, Oya Kalipsiz; Tekirdağ Namik Kemal University, Çorlu Faculty of Engineering, Department of Computer Engineering, Tekirdağ, Turkey. 2019.

Big Data Analytics and Precision Animal Agriculture Symposium: Data to decisions B. J. White, D. E. Amrine, and R. L. Larson Beef Cattle Institute, Kansas State University, Manhattan, KS; © the Author(s) 2018. Published by Oxford University Press on behalf of American Society of Animal Science.

Gasteiner, J.; Boswerger, B.; Guggenberger, T., Practical use of a novel ruminal sensor on dairy farms, Praktische Tierarzt 2012 vol. 93 No. 8 po. 730 . . . 739 ref.45.

Drying up Cows and the Effect of Different Methods Upon Milk Production; Ralph Wayne, C. H. Eckles, and W. E. Peterson; Division of Dairy Husbandry, University of Minnesota, St. Paul; Research-Article| vol. 16, Issue 1, p. 69-78, Jan. 1, 1933.

\* cited by examiner

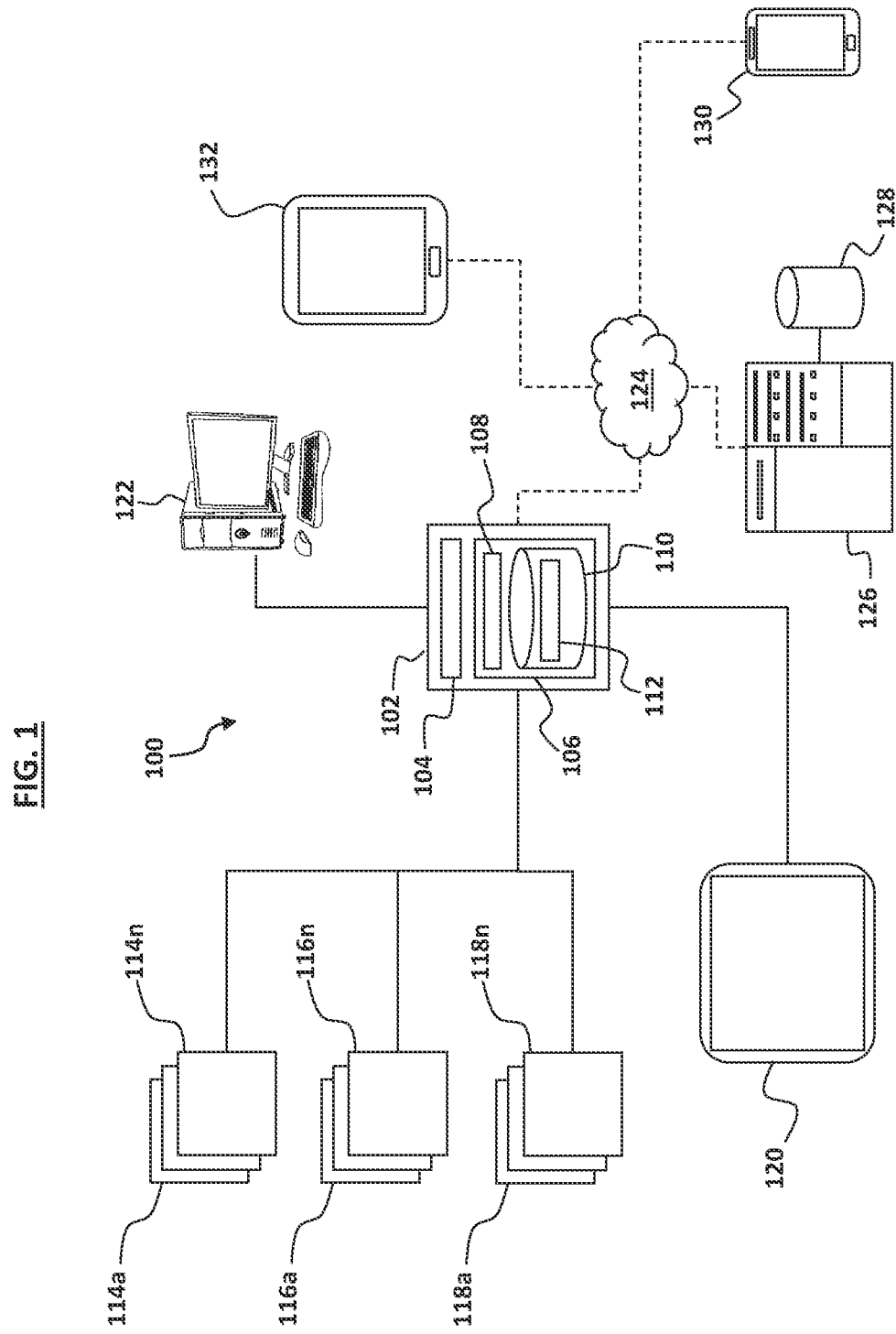

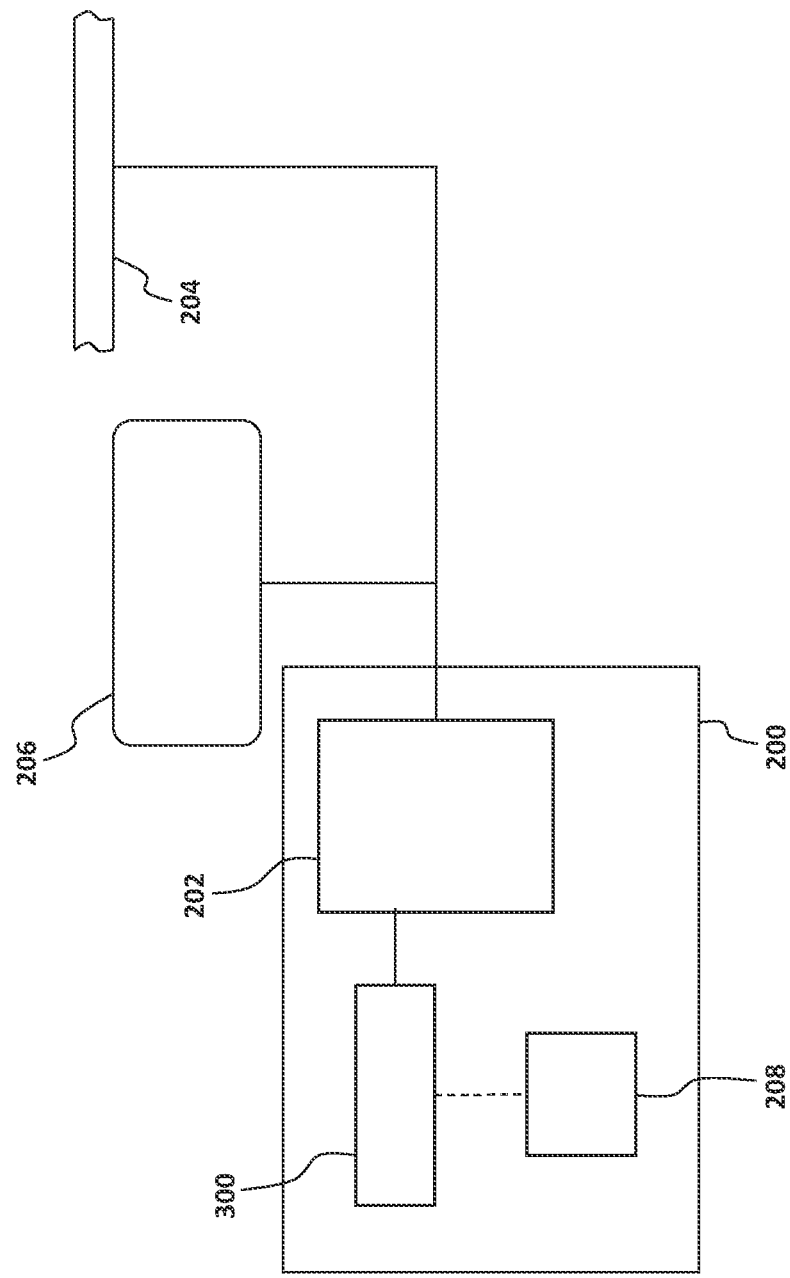

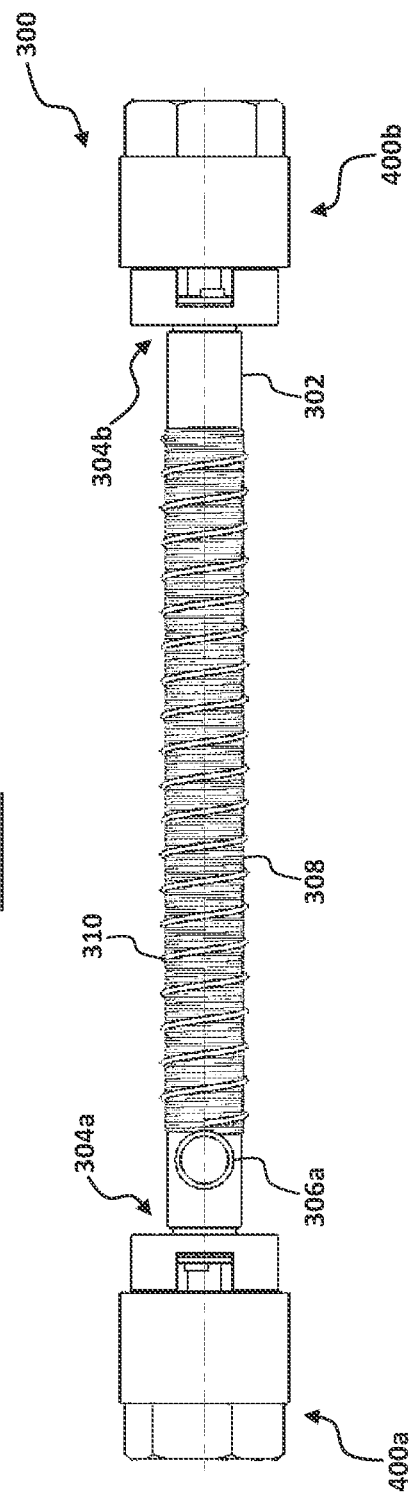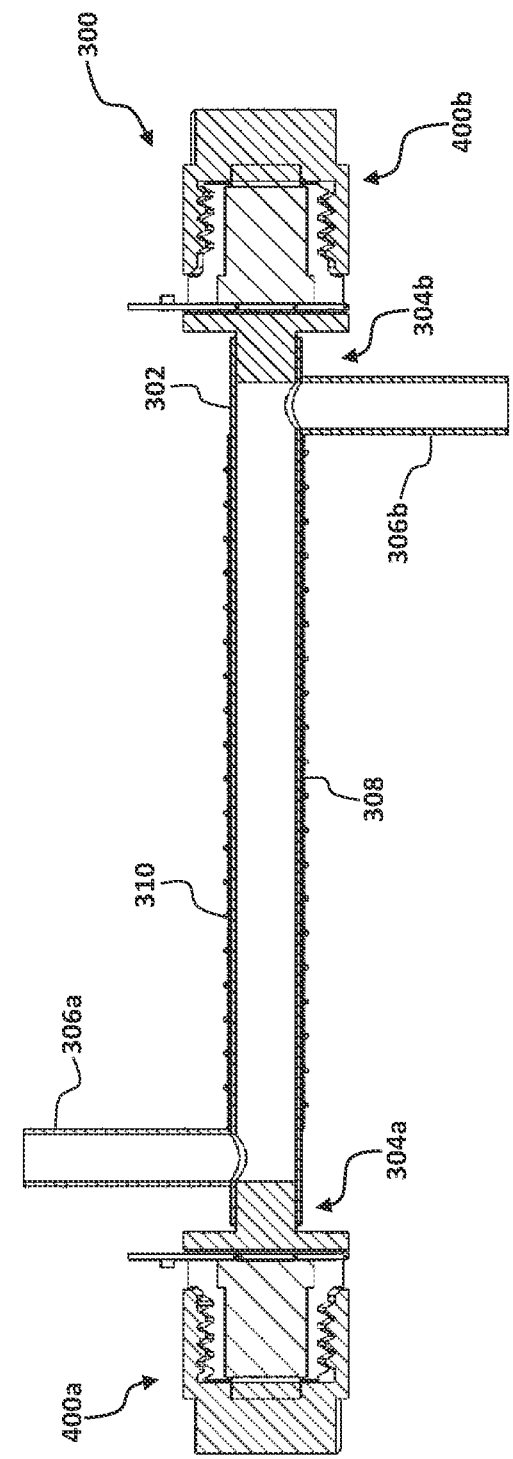

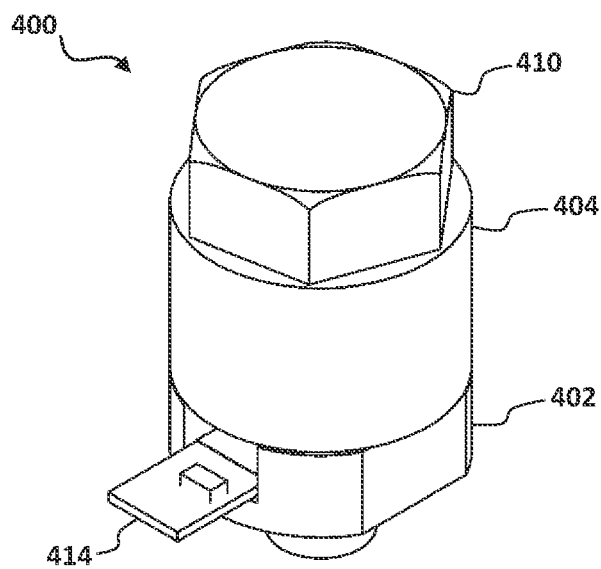
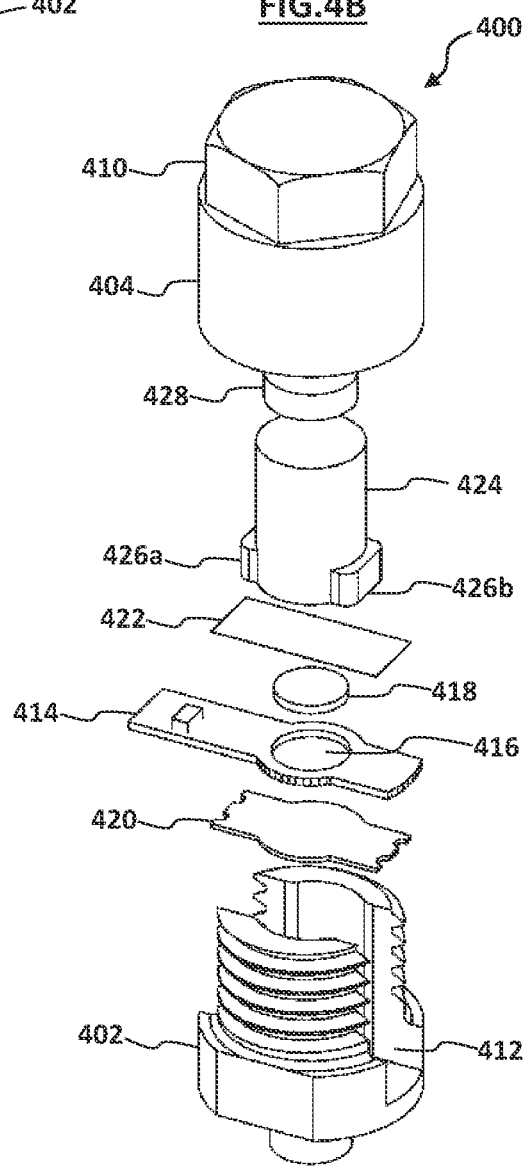

DEVICES FOR ANALYSIS OF A FLUID

STATEMENT OF CORRESPONDING APPLICATIONS

This application is based on the provisional specification filed in relation to New Zealand Patent Application No. 756776, the entire contents of which are incorporated herein by reference.

TECHNICAL FIELD

The present disclosure relates to analysis of a fluid—more particularly ultrasound transducers for use in analysis of milk.

BACKGROUND

The use of sensors to obtain information relating to milk collected from dairy animals is well known. Such information is used in decision making regarding such matters as processing of the milk, culling, breeding, medical treatment, animal specific feed rations as well as measurement of milk production efficiency.

Numerous portable off-line analysers are known in the art for analysing a sample of milk to determine parameters such as fat, protein, lactose and total solids. Examples of such analysers using ultrasound analysis include the Lacti-Check™ milk analyser by Page & Pedersen International, Ltd (www.pagepedersen.com); the Master milk analyser by Milkotester Ltd (www.milkotester.com); and the LACTOSCAN™ milk analyser by Milkotronic Ltd (www.lactoscan.com).

Such off-line analysers are generally capable of relatively high precision measurements in comparison with commercially available in-line sensors. However, they have practical limitations associated with the collection of samples for analysis — requiring an operator to collect and deliver samples to the sensor.

Sensors of other types are known for use in milking systems whereby samples are automatically extracted from the system for analysis. However, known ultrasound-based analysers are not well suited to this application, i.e. being fluidly connected to the milking system. For example, sensor having a measuring cell and one or more transducers needs to be suitable for exposure to milk as well as chemicals commonly used in cleaning milking systems. However, material selection for such an interface needs to be weighed against costs, and the ultrasonic transmission and acoustic impedance characteristics of the material.

It is an object of the present invention to address the foregoing problems or at least to provide the public with a useful choice.

Further aspects and advantages of the present invention will become apparent from the ensuing description which is given by way of example only.

SUMMARY

The present disclosure provides ultrasound transducers, ultrasound sensor devices utilising said transducers, and systems for analysing a fluid sample.

According to one aspect of the present disclosure, there is provided an ultrasonic transducer including a piezoelectric element, a fluid medium contact layer, a matching layer between the piezoelectric element and the fluid medium contact layer, and a backing layer.

Arrangements and material properties of the elements of the transducer are provided for obtaining desired performance characteristics. Generally, it is envisaged that such arrangements may be used to reduce reflections of acoustic signals at material boundaries, or combinations of boundaries, with the objective of attaining a transducer performance for transmitting signals into, and receiving signals from, the sample with a near ideal damped characteristic as viewed in the time and frequency domains.

More particularly, it is envisaged that the exemplary embodiments of the present disclosure may be used in sensing a characteristic of milk and/or water, where the nominal acoustic impedance of milk is 1.56 Mrayl, while the nominal acoustic impedance of water is 1.49 MRayl. However, it should be appreciated that exemplary embodiments of the present disclosure may be used in the sensing of other fluids, particularly food or medical products. In examples, the fluid may be non-gaseous. In examples, the fluid may be a liquid. In examples the fluid may be a solution comprising solids suspended in a liquid, such as a slurry.

It is envisaged that as the impedance of the fluid increases towards that of the fluid medium contact layer, the energy transmitted at that boundary may increase. The inverse is also to be expected for lower impedance fluids, but while less transmitted energy and relatively more reflected energy can be expected, it is envisaged that a useful measurement may still be obtained. By way of example, ethanol (nominal acoustic impedance of 0.95 MRays) and honey (nominal acoustic impedance of 2.89 MRayls) are envisaged as being plausible measurement mediums for use with the transducer.

In an exemplary embodiment the piezoelectric element may be one or more of:
  a lead metaniobate piezoelectric element;
  a piezoelectric element having an acoustic impedance of between 15 to 22 MRayls.

Lead metaniobate is a commercially available piezoceramic material that has a relatively low acoustic impedance in comparison with other piezoceramic materials such as lead zirconate titanates (PZT). It is envisaged that this relatively low impedance may assist with reducing the impedance gap between the piezoelectric element, and the fluid medium contact layer. Further, this may assist with provision of a backing layer having a comparable acoustic impedance. Other piezoelectric materials are available (e.g. piezocomposites) that have relatively low impedance values and may be used in exemplary embodiments of the present disclosure, but it is envisaged that lead metaniobate may have particular application to embodiments in which limiting cost is a high priority consideration. In an exemplary embodiment, the lead metaniobate may be APC 3285 (available from APC International).

In an exemplary embodiment the fluid medium contact layer may be one or more of:
  a polymer layer;
  a fluid medium contact layer having an acoustic impedance of between 2.5 to 3.5 MRayls.

In an exemplary embodiment in which the fluid medium contact layer is a polymer layer, the polymer may be polysulfone. Polysulfone is generally characterised by properties well suited to the milking system environment such as chemical inertness, toughness, and thermal stability. Polysufone has an acoustic impedance in the order of 2.78 MRayl, being relatively close to that of the fluid medium (e.g. milk or water) in comparison with other materials and thereby reducing reflections at the boundary between the contact layer and the fluid medium. Polysufone also has suitable acoustic transmission properties in addition to the aforementioned properties, reducing attenuation in comparison with other materials. Polysufone is also considered to be suitable for use in exemplary embodiments of the present disclosure in terms of price point, and ability to be machined or molded.

It should be appreciated that reference to the polymer layer consisting of polysulfone is not intended to be limiting to all embodiments of the present disclosure. By way of example, it is envisaged that the polymer may be an amorphous polyamide (such as the Grilamid TR 90 product available from EMS Group)—particularly where intended for use in or with milking systems. It should also be appreciated that in exemplary embodiments the polymer layer may be a composite material, or a polymer with a non-polymer filler.

In an exemplary embodiment, the thickness of the fluid medium contact layer may be configured to delay reflections of an acoustic signal from an interface between the fluid and the fluid medium contact layer by a predetermined number of wavelengths, or part wavelengths, of the acoustic signal. Reference to the thickness of the fluid medium contact layer should be understood to mean the dimension in the direction between the piezoelectric element and the fluid and contact layer interface. It is envisaged that there may be some mismatch of acoustic impedance at this interface as the result of other design constraints, resulting in reflections that may have an effect on signal detection and analysis. Delaying the reflections is expected to reduce their influence—i.e. received by the piezoelectric element after the majority of ringing from a pulse signal has died down.

In an exemplary embodiment the number of wavelengths for the delay may be at least four. As such, the thickness of the fluid medium contact layer may be at least two wavelengths (such that the total path length is four wavelengths) of the acoustic signal—more particularly two wavelengths at a low frequency cut-off of the design bandwidth.

In another exemplary embodiment the thickness of the fluid medium contact layer may be about one quarter wavelength in length (e.g. between 0.2 to 0.3 wavelength) in order to provide a quarter wave matching effect as described below in relation to the matching layer.

In an exemplary embodiment the matching layer may be one or more of:
 a hydrocarbon ceramic laminate layer;
 a matching layer having an acoustic impedance of between 4 to 10 MRayls;
 a circuit board layer having an acoustic impedance of between 4 to 10 MRayls.

It should be appreciated that reference to a matching layer in the context of an ultrasound transducer is intended to mean an intermediate layer provided for reducing energy reflected between two materials in the acoustic path—more particularly, the piezoelectric element and the fluid medium contact layer.

For this geometry with a harmonic plane wave at normal incidence, standard formulations exist for the transmission coefficient of acoustic energy from the piezoelectric element and the fluid contact layer (and vice-versa). These formulations show that when the thickness of the matching layer equates to ¼ wavelength within that material and $Z_0 = \sqrt{(Z_1 \cdot Z_2)}$, where $Z_0$ is the acoustic impedance of the matching layer with $Z_1$ and $Z_2$ being the acoustic impedances of the piezoelectric element and fluid contact layer, the transmission coefficient will be maximised and the frequency response approach that of an ideal damped transducer.

It is envisaged that a matching layer impedance of between 4 to 10 MRayls may be suitable in exemplary embodiments of the present disclosure. In an exemplary embodiment the matching layer may have an acoustic impedance of between 5 to 8 MRayls.

In exemplary embodiments in which the matching layer is a circuit board layer, it is envisaged that the matching layer may provide electrical connections to the piezoelectric element—i.e. in addition to its function in matching acoustic impedance between the piezoelectric element and the fluid medium contact layer.

In an exemplary embodiment in which the matching layer is a hydrocarbon ceramic laminate, the hydrocarbon ceramic laminate may be a laminate such as the RO4000 series (available from Rogers Corporation), and more particularly RO4003C or an equivalent thereof.

In addition to having a suitable acoustic impedance for use in exemplary embodiments of the present disclosure, being in the order of 6 MRayls, this material is fabricated with a copper layer (by way of electrodeposited copper foil) for PCB applications and has a construction more suitable to use in the present disclosure than other circuit board materials. A typical PCB fibreglass construction would tend to scatter the ultrasound signal, with associated losses. In contrast, the RO4000 material has a smaller grain size and thinner fibreglass reinforcing, with scattering being reduced as a result.

In an exemplary embodiment, the thickness of the matching layer may provide quarter wave matching with the ultrasound signal. More particularly, the thickness of the matching layer may be between 20 to 30% of the signal wavelength at the centre frequency of the transducer (i.e. between 0.2 to 0.3 wavelengths of the acoustic signal). It should be appreciated that it may be generally desirable for the thickness of the matching material to have low variability in order to achieve this design parameter. In addition to the other properties described herein, the RO4000 material is considered to have a highly controlled thickness. For example, the RO4003 material used in exemplary embodiments of the present disclosure is available in a standard thickness of 0.203 mm, which approximates a quarter wavelength at a centre frequency of about 3.75 MHz.

It should be appreciated that while the matching layer may be a single layer of material, in exemplary embodiments the matching layer may include two or more layers. However, control of the thickness of each of the layers becomes particularly important, and consequently the cost for implementing more than one matching layer can be unnecessarily high.

It should be appreciated that alternative materials may be used for the matching layer in exemplary embodiments—for example, an alumina composite.

In an exemplary embodiment the backing layer may be one or more of:
 a backing layer having an acoustic impedance substantially that of the piezoelectric element;
 a backing layer having an acoustic impedance of between 15 to 20 MRayls; and
 a tungsten composite layer.

The backing layer forms part of the acoustic path for ultrasound energy directed backwards from the piezoelectric element. It is considered desirable that the acoustic signal that propagates into the backing layer be rapidly absorbed—i.e. any acoustic signal propagating through the piezoelectric element, including that resulting from transmission excitation, does not reverberate for an extended period. More particularly, the ultrasound energy directed backwards from the piezoelectric element should essentially not return, being diminished in magnitude to substantially less than the forward going acoustic energy at that time (for example, by an order of magnitude).

In an exemplary embodiment in which the backing layer is a tungsten composite layer, the tungsten composite may include tungsten particles of a first size, and tungsten particles of a second size. It is envisaged that this may assist with improving the ability of the backing layer to absorb the acoustic signal over a broader range of frequencies in comparison with a single particle size. Further, the relatively high density of tungsten is considered to aid in achieving a suitable acoustic impedance.

In an exemplary embodiment, the larger particle may be a granulated tungsten powder—such as that made by crushing of sintered tungsten metal (for example GW-100270 available from Buffalo Tungsten Inc). In an exemplary embodiment, the smaller particle may be a fine tungsten powder (for example C20-491 available from Buffalo Tungsten Inc). It should be appreciated that the ratio of the two particle sizes may be adjusted according to the desired acoustic properties of the backing layer; in an exemplary embodiment the ratio may be in the order of 56:7 of the granulated powder to fine powder. It should be appreciated that the backing layer may include a suspension medium for the tungsten particles—for example, an epoxy resin.

In an exemplary embodiment the backing layer may be manufactured using a centrifuge, such that there is a graduation in the density in the suspended particles due to the forces imparted by the centrifuge. It is believed that this graduation of density, and so a graduation in impedance, along the length of the backing layer may aid attenuation.

According to one aspect of the present technology, an ultrasound transducer constructed in accordance with exemplary embodiments of the present disclosure may have one or more of: a centre frequency of between 1 to 10 MHz; a centre frequency of between 3 to 5 MHz; a centre frequency of between 3.5 to 4 MHz; and a centre frequency of about 3.75 MHz.

Attenuation of ultrasound signals in a medium such as milk increases with frequency. As such, it is considered generally desirable to avoid a higher centre operating frequency, as this would require more energy to achieve a received signal of sufficient strength. It is also believed that higher frequency signals may also complicate the electronics design of associated circuitry of sensors utilizing the transducer(s), with associated issues in terms of cost and reliability. Higher frequencies may also require the design of the piezoelectric element and matching layer to be thinner, where complications in manufacture begin to arise due to the accuracy required, as well as becoming unsuitably fragile for assembly. Additionally, where adhesive is applied between layers, it is considered desirable for the thickness of the adhesive to be much less than a wavelength—at higher frequencies tighter tolerances are required for the surface finish of each of the mating surfaces to reduce discontinuities resulting from adhesive filling voids in the surfaces.

Conversely, at lower design frequencies, the axial dimensions of key acoustic components will increase in large part in relation to the wavelength. Additionally, the attenuation of the acoustic signal propagating in the backing layer is significantly sensitive to frequency, as it is in part related to wave scattering. As a result, it is harder to attain backing performance at lower frequency. Generally speaking, a lower centre frequency will result in a lower resolution in time, and it is desirable to balance this effect against those associated with higher frequencies.

For completeness, it should be appreciated that the centre frequency of the transducer is the cumulative result of the characteristics of the various layers (e.g. the piezoelectric element, fluid contact layer, matching layer and backing layer), and that the centre frequency may be adjusted accordingly by modification of these characteristics.

According to one aspect of the present technology, an ultrasound transducer constructed in accordance with exemplary embodiments of the present disclosure may have one or more of:
  a −6 dB percentage bandwidth greater than 60%;
  a −6 dB percentage bandwidth of between 60% to 100%;
  a −6 dB bandwidth between 2 to 3 MHz.

Bandwidth may be measured using a standard by which a narrow width pulsatile voltage is applied to the transducer to launch an ultrasonic wave. Either a second transducer may be used to detect this wave, or the transducer configured so the launched wave reflects and is detected by the same transducer. In both instances the received voltage is recorded and used to characterise the transducer performance.

The ultrasound transducer requires sufficient bandwidth to achieve a desired resolution, more particularly temporal resolution of the acoustic signal propagation time through the fluid sample.

Ultrasound transducers with a relatively narrow frequency response will produce a pulse containing several cycles, reducing the resolution. Conversely, a relatively wide frequency response provides a higher degree of damping which produces a shorter pulse in the time domain, resulting in higher resolution. However, performance in terms of resolution needs to be weighed against practical constraints such as costs and availability of piezoelectric elements having such characteristics. Manufacturing of such components requires more sophisticated processing techniques, with associated costs which are a significant barrier to their adoption in applications such as sensors for on-farm milk analysis. The technology of the present disclosure seeks to strike a balance between a desired level of performance in terms of resolution, and costs which might otherwise prohibit adoption of the technology.

In an exemplary embodiment, the ultrasound transducer may include a housing. In an exemplary embodiment the housing may include a main body. In an exemplary embodiment, a portion of the main body may provide the fluid medium contact layer.

In an exemplary embodiment the main body may include a projection through which the acoustic pathway of the transducer passes. It is envisaged that the projection may take the form of a solid cylindrical shaft, with a free end of the shaft providing a flat surface intended to face the fluid to be sensed in use.

In exemplary embodiments the acoustic velocity in the material of the body, and therefore fluid medium contact layer, may be temperature dependent. It is contemplated that the temperature of the material may vary between measurements, and also vary more significantly that the fluid being sensed. The effect of this will depend on a number of factors, for example shaping of components of the transducer, insulation, temperature range experienced, and signal power input. However, it is envisaged that the shaft length, from the matching layer to the flat surface, may alter the extent to which ambient temperature effects sound speed measurements of the fluid. The fluid medium contact layer is exposed to ambient conditions, and also receives varying heat inputs from the piezoelectric element and other heating sources. This means that the temperature of the fluid medium contact layer may take longer to stabilise than the fluid, and may stabilise at different temperatures depending on the ambient conditions. Rather than control the temperature of the fluid medium contact layer, it is envisaged that this influence may be contained by reducing the length of the fluid medium contact layer as a percentage of the overall acoustic path length. In an exemplary embodiment in which two opposing transducers are used in an ultrasound sensor device, the length of the fluid medium contact layer may be less than 15% of the overall path length. Increasing the separation between transducer, or decreasing the length of the fluid medium contact layer, can further reduce the percentage if greater accuracy or wider ambient temperature ranges are required.

In an exemplary embodiment the housing may include a cap, configured to be secured to the main body. It is envisaged that the cap and main body may include complementary threads—but it should be appreciated that this is not intended to be limiting. For example, the cap and main body may be secured using one or more of: an interference fit, clips, fasteners, or any other suitable means known in the art.

In an exemplary embodiment the ultrasound transducer may have a piezoelectric assembly including the piezoelectric element and the matching layer.

In an exemplary embodiment the piezoelectric assembly may include an element holder. The element holder may include an aperture in which the piezoelectric element is located. In an exemplary embodiment the element holder may be made of a circuit board material.

In an exemplary embodiment the matching layer may span the aperture of the element holder. In exemplary embodiments the matching layer may provide an electrical contact to the piezoelectric element—for example, where the matching layer is a circuit board.

In an exemplary embodiment the piezoelectric assembly may include an electrical contact on the other side of the piezoelectric element from the matching layer. In an exemplary embodiment, the electrical contact may include a foil strip—for example a copper foil in the order of 35 μm or less in thickness. In an exemplary embodiment the foil may be arranged to span the aperture of the element holder and contact an entire face of the piezoelectric element. It is envisaged that the foil strip may be soldered to the element holder. It is envisaged that the foil thickness may be selected to provide a degree of robustness during assembly, but not be so thick so as to significantly influence the acoustic path to the backing layer.

In an exemplary embodiment one or more electronic components may be provided on the element holder.

In an exemplary embodiment, the housing body and/or piezoelectric assembly may be configured so as to locate the piezoelectric assembly in a desired position and orientation during assembly of the transducer. For example, the housing body may include a receiving portion configured to receive the piezoelectric assembly and shaped to restrict movement — particularly rotation or lateral movement.

According to one aspect of the present disclosure there is provided an ultrasound sensor device, including: a hollow body configured to receive a fluid to be analysed, a first ultrasound transducer, and a second ultrasound transducer.

In an exemplary embodiment the hollow body may be elongate. For example, it is envisaged that the hollow body may be a tube.

In an exemplary embodiment the first and second ultrasound transducers may be arranged to face each other through the hollow body. In exemplary embodiments in which the hollow body is elongate the transducers may be disposed at distal ends of the hollow body.

In an exemplary embodiment, the hollow body may be made of a metal. In an exemplary embodiment the hollow body may be made of a stainless steel.

In ultrasound-based measuring cells used in off-line sensing of milk, the body is typically made of brass, which has a high heat transfer coefficient and can be constructed with a very thin wall, allowing it to quickly and precisely control milk temperature. However, brass is not resistant to the acidic chemicals commonly used in cleaning milking systems. The use of stainless steel may assist with providing resistance to such chemicals, enabling cleaning of the device using chemicals already in use within the wider system. This has further implications for assembly, as brass material allows the prior art ultrasonic transducer assemblies to be secured together, and to the measuring cell, in a relatively simple and robust way using solder. However, a solder-based assembly method is incompatible with materials such as stainless steel and polysulfone. As such, features of the present disclosure are intended to facilitate assembly of the transducer, and the ultrasound sensor device using the transducer, with one or more of the following considerations in mind: repeatability, secure and robust construction, achieving electrical connection to the piezoelectric element with insignificant impact on the acoustic performance, and doing so with the general constraints of cost containment and material suitability for milk contact.

According to one aspect of the present disclosure there is provided an ultrasound sensor device, including: a hollow body having an acoustically reflective surface and being configured to receive a fluid to be analysed, and a first ultrasound transducer facing the acoustically reflective surface.

In exemplary embodiments the path length between piezoelectric elements of respective ultrasound transducers, or the total return path length between the piezoelectric element of an ultrasound transducer and the acoustically reflective surface, may be one of: greater than about 25 mm; between 25 mm to 100 mm; between 50 mm to 80 mm; greater than about 50 mm; between 60 mm to 75 mm; and about 70 mm. It is envisaged that such embodiments may be particularly applicable to embodiments in which the hollow body is tubular, and for use cases in which the fluid is milk.

According to one aspect of the present disclosure there is provided a system for analysing a fluid, including: a ultrasound sensor device; a sample delivery device configured to deliver a sample of fluid from a fluid carrying and/or storing system to the ultrasound sensor device; and at least one processor configured to determine a characteristic of the sample of fluid based at least in part on a signal output from the ultrasound sensor device.

In exemplary embodiments, the fluid may be milk extracted from a milking animal. It is envisaged that the present disclosure may have particular application to the analysis of milk during the transfer of milk from the point of extraction to a storage vessel. Milking systems typically include individual milk transport conduits from the points of extraction (for example, using a milking cluster including teat cups), joining to a common transport line for delivery to the storage vessel.

In exemplary embodiments, the system may be embodied in a single unit—which may be referred to herein as a sensor. Various configurations of sensors, in terms of how the sensor is exposed to the fluid to be analysed, are known in the art. Terms such as "in-line", "on-line", "at-line", "near-line" and "off-line" are used in the art to distinguish between these configurations—however there is a degree of inconsistency in their usage. For clarity, reference to an on-line sensor should be understood to mean a sensor which automatically extracts a sample of fluid from a fluid source (for example, a milk line or jar in the context of milking systems), and analyses the sample of fluid to determine at least one characteristic of the sample. As used herein, the term "on-line" may encompass embodiments in which the sample is returned to the source, or discarded. The terms "at-line" and "off-line" may be used in the art to distinguish between the environment in which the sensor is configured to operate. Both at-line and off-line sensors are configured to analyse a discrete sample of the fluid delivered to the sensor by an operator. At-line sensors (which may be referred to as "near-line" sensors) are generally intended to be located within the vicinity of the fluid source—for example, within a milking facility—while off-line sensors are primarily intended for use in a more environmentally controlled environment—for example, in a laboratory. In practice, particularly for milking operations, analysis of a sample by an off-line sensor may necessitate transport of the sample from the sample source to a remote facility. As used herein, the term "off-line" should be understood to refer to a sensor configuration in which a sample is collected from the fluid, and delivered to the sensor by an operator rather than an automated system. On-line and off-line sensors, as defined herein, may be distinguished from in-line sensors by the act of analysing a sample extracted from the fluid rather than analysing the flow itself. As such, on-line and off-line sensors may be referred to in the collective as "sample" sensors.

BRIEF DESCRIPTION OF DRAWINGS

Further aspects of the present invention will become apparent from the following description which is given by way of example only and with reference to the accompanying drawings in which:

FIG. 1 is a schematic diagram of an exemplary livestock management system in which an aspect of the present disclosure may be implemented;

FIG. 2 is a schematic diagram of an exemplary on-line sensor according to one aspect of the present disclosure;

FIG. 3A is a top view of an exemplary ultrasound sensor device according to one aspect of the present disclosure;

FIG. 3B is a side cross-section view of the ultrasound sensor device;

FIG. 4A is a perspective assembled view of an exemplary ultrasound transducer according to one aspect of the present disclosure;

FIG. 4B is a perspective exploded view of the ultrasound transducer;

DETAILED DESCRIPTION

Figure 4C:
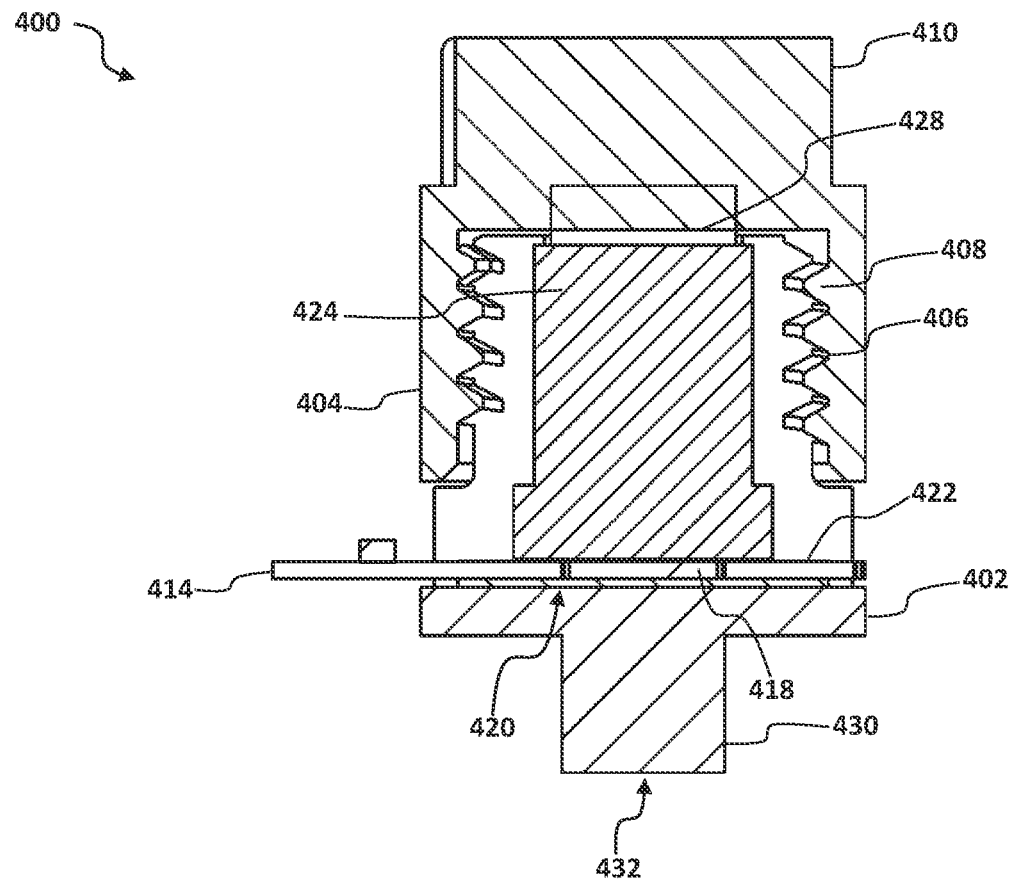
FIG. 4C is a side cross-sectional view of the ultrasound transducer.

Exemplary embodiments are discussed herein in the context of analysis of milk. However, it should be appreciated that principles of the disclosure discussed herein may be applied to the analysis of other fluids.

FIG. 1 illustrates a livestock management system 100, within which a local hardware platform 102 manages the collection and transmission of data relating to operation of a milking facility. The hardware platform 102 has a processor 104, memory 106, and other components typically present in such computing devices. In the exemplary embodiment illustrated the memory 106 stores information accessible by processor 104, the information including instructions 108 that may be executed by the processor 104 and data 110 that may be retrieved, manipulated or stored by the processor 104. The memory 106 may be of any suitable means known in the art, capable of storing information in a manner accessible by the processor 104, including a computer-readable medium, or other medium that stores data that may be read with the aid of an electronic device. The processor 104 may be any suitable device known to a person skilled in the art. Although the processor 104 and memory 106 are illustrated as being within a single unit, it should be appreciated that this is not intended to be limiting, and that the functionality of each as herein described may be performed by multiple processors and memories, that may or may not be remote from each other. The instructions 108 may include any set of instructions suitable for execution by the processor 104. For example, the instructions 108 may be stored as computer code on the computer-readable medium. The instructions may be stored in any suitable computer language or format. Data 110 may be retrieved, stored or modified by processor 104 in accordance with the instructions 108. The data 110 may also be formatted in any suitable computer readable format. Again, while the data is illustrated as being contained at a single location, it should be appreciated that this is not intended to be limiting—the data may be stored in multiple memories or locations. The data 110 may also include a record 112 of control routines for aspects of the system 100.

The hardware platform 102 may communicate with various devices associated with the milking facility, for example: in-line sensors 114a to 114n associated with individual milking clusters within the milking facility, and sample sensors in the form of on-line sensors 116a to 116n associated with the individual milking clusters or milk jars collecting milk from same.

Animal identification devices 118a to 118n are provided for determining an animal identification ("animal ID") of individual animals entering, or within, the milking facility. More particularly, the animal identification devices 118a to 118n may be used to associated an animal ID with each of the milking clusters associated with the in-line sensors 114a to 114n and on-line sensors 116a to 116n, such that the sensor data may be attributed to the individual animals. A variety of methodologies are known for the determination of an animal ID—for example a radio frequency identification ("RFID") reader configured to read a RFID tag carried by the animal. In an alternative embodiment, or in conjunction with the animal identification devices 118a to 118n, a user may manually enter (or correct) animal IDs via a user device—examples of which are discussed below.

The hardware platform 102 may also communicate with user devices, such as touchscreen 120 located within the milking facility for monitoring operation of the system, and a local workstation 122. The hardware platform 102 may also communicate over a network 124 with one or more server devices 126 having associated memory 128 for the storage and processing of data collected by the local hardware platform 102. It should be appreciated that the server 126 and memory 128 may take any suitable form known in the art—for example a "cloud-based" distributed server architecture. The network 124 potentially comprises various configurations and protocols including the Internet, intranets, virtual private networks, wide area networks, local networks, private networks using communication protocols proprietary to one or more companies—whether wired or wireless, or a combination thereof. It should be appreciated that the network 124 illustrated may include distinct networks and/or connections: for example a local network over which the user interface may be accessed within the vicinity of the milking facility, and an internet connection via which the cloud server is accessed. Information regarding operation of the system 100 may be communicated to user devices such as a smart phone 130 or a tablet computer 132 over the network 124.

Referring to FIG. 2, an exemplary sensor 200 is illustrated, which may be used (for example) as one or more of the on-line sensors 116a to 116n. In this exemplary embodiment, the on-line sensor 200 includes an ultrasound sensor device 300, configured to perform ultrasound-based measurements of milk contained therein.

The sensor 200 includes sample delivery device 202 configured to be connected to a source of the fluid to be sampled—for example milk tube 204 or milk jar 206—and deliver a sample of the fluid to the ultrasound sensor device 300.

A controller 208 is provided to control the operation of the various components described, receive data obtained by the ultrasound sensor device 300, and communicate over a network such as the network 124.

FIG. 3A and FIG. 3B illustrate an exemplary embodiment of the ultrasound sensor device 300. The sensor device 300 includes a hollow body in the form of a stainless steel main tube 302, having a first end 304a and a second end 304b. A first port tube 306a is provided proximate the first end 304a, while a second port tube 306b is provided proximate the second end 304b. In this exemplary embodiment, the port tubes 306 extend radially from the main tube 302 in opposing directions. In use, the port tubes 306 function as an inlet/outlet to and from the main tube 302.

Between the port tubes 306, the exterior of the main tube 302 may be wrapped in coiled heating wires, for example an enamelled fine copper winding 308 around the main tube 302, and a larger nichrome wire winding 310 coiled over the copper winding 308. While not illustrated, it is envisaged that at least the copper windings 308 may also be provided on the port tubes 306. The respective windings 308 and 310 may be connected in series, and current supplied to control temperature of the sensor device 300 and/or fluid being sensed. Further, the resistance of the windings 308 and/or 310 may be used to determine temperature. While not illustrated, it is also envisaged that insulating material may be provided over at least the main tube 302 in order to reduce the influence of ambient temperature and/or to increase efficiency when heating the fluid to measurement temperatures. It is envisaged that the insulating material may not cover the ends of the sensor device 300 to allow for heat dissipation from a first ultrasound transducer 400a at the first end 304a of the main tube 302, and a second ultrasound transducer 400b at the second end 304b.

The first ultrasound transducer 400a and the second transducer 400b are arranged to face each other along the longitudinal axis of the main tube 302. In use, one of the transducers 400 is configured as a transmitter, while the other is configured as a receiver.

FIG. 4A to 4C illustrate an exemplary embodiment of the ultrasound transducer 400. The transducer 400 includes a housing having a main body 402 and a cap 404 configured to be secured to the main body 402. Referring to FIG. 4C, the main body 402 includes a first set of threads 406, while the cap 404 includes a second set of threads 408 configured to engage the first set of threads 406. The cap 404 includes a tool engaging portion, for example hexagonal head 410. In this exemplary embodiment, the housing is made of polysulfone, as will be discussed further below.

Referring to FIG. 4A, the main body 402 includes a slotted portion 412 configured to receive components of the transducer 400. In the exemplary embodiment illustrated, a piezoelectric element holder (referred to herein as piezo holder 414) is provided, having an aperture 416 configured to receive a piezoelectric element 418. In this embodiment, the piezoelectric element 418 is a disk-shaped lead metaniobate piezoelectric element. The acoustic impedance of the piezoelectric element 418 is between 15 to 22 MRayls, more particularly in the order of 16 MRayls. In an exemplary embodiment the piezoelectric element is constructed of 0.5 mm thick APC3285. When heavily damped in the exemplary transducer design the resulting transducer has a centre frequency around 3.75 MHz.

In this embodiment, the piezo holder 414 is made of a circuit board material for ease of forming electrical connections. The piezo holder 414 includes a rigid portion for locating the piezoelectric element 418 and an elongate flex portion 504 to act as an electrical connection. A piezoelectric contact member (referred to herein as piezo contact 420) is provided beneath the piezo holder 414 to contact the piezoelectric element 418. In this embodiment, the piezo contact 420 is made of RO4003C with a 35 μm electrodeposited copper foil layer, available from Rogers Corporation. In this exemplary embodiment, an electrical contact is provided on the opposing side of the piezo holder 414 (to the piezo contact 420) in the form of a foil strip 422—for example, a copper foil in the order of 33 μm in thickness.

Above the foil strip 422, a backing element 424 is provided. The backing element 424 is generally cylindrical in shape, having locating wings 426a and 426b on opposing sides. The locating wings 426 align with the slotted portion 412 of the main body 402, to assist with maintaining the position of the backing element 424 during assembly. A PTFE gasket 428 is provided between the backing element 424 and the cap 404.

Referring to FIG. 4C, below the piezo contact 420 the main body 402 includes a cylindrical shaft 430. The distal end of the shaft 430 has a flat surface 432, which in use is presented to the interior of the main tube 302 (as shown in FIG. 3B). The thickness of the main body 402 from the flat surface 432 to the piezo contact 420 is influenced by several factors. Firstly, the temperature of polysulfone has an effect on acoustic performance (more particularly sound speed), and the main body 402 is subject to heat inputs from the piezoelectric element 418 and windings 308 and 310, as well as fluctuations in the ambient temperature. Secondly, reflections of the acoustic signal will occur at the boundary between the flat surface 432 and the fluid, which if not accounted for will interfere with signal analysis. As such, there is a balance to be struck between reducing the thickness of the polysulfone as a percentage of the overall signal transmission path, and achieving a sufficient thickness so as to delay the reflections.

Further, there are practical considerations for assembly of the transducer 400—for example, the shaft 430 being of a sufficient length for fitting to the main tube 302 of the sensor device 300. It should also be appreciated that the diameter of the shaft 430 may be sized relative to the internal diameter of the main tube 302 to produce a seal, as well as mechanically securing the transducer 400 to the main tube 320.

In the exemplary embodiment illustrated in FIG. 3A and 3B, the respective piezoelectric elements of the transducers 400a and 400b are spaced apart at 69 mm (comprising a 59 mm gap between end surfaces, and a polysulfone thickness of about 5 mm). The thickness of the polysulfone of each transducer 400 is about 5 mm, which in combination represents just under 15% of the total path length. It is also considered desirable for reflections to be delayed by at least four wavelengths—i.e. requiring the thickness of the polysulfone to be at least two wavelengths. In a design having a 2.5 MHz low frequency cut-off, and 2240 m/s nominal sound speed in polysulfone, the wavelength of the signal through the main body 402 is 0.896 mm. A 5 mm thickness provides a total path length of eleven wavelengths, which satisfies this design criteria.

With the acoustic impedance of the piezoelectric element being in the order of 16 MRayls, it is desirable for the acoustic impedance of the backing element 424 to be substantially the same. In the exemplary embodiment described herein, the backing element 424 is made of a tungsten composite, including tungsten particles of a relatively large size (more particularly granulated tungsten powder—such as GW-100270 available from Buffalo Tungsten Inc), and tungsten particles of a relatively small size (more particularly fine tungsten powder—such as C20-491 available from Buffalo Tungsten Inc). It is envisaged that this may assist with improving the ability of the backing element to absorb the acoustic signal over a broader range of frequencies in comparison with a single particle size. Further, the relatively high density of tungsten is considered to aid in achieving a suitable acoustic impedance. In this exemplary embodiment, the tungsten particles are suspended in an epoxy resin, for example EpoTek 301 available from Epoxy Technology Inc. In an exemplary embodiment, the ratio of GW-100270:C20-491:EpoTek 301A may be in the order of 56:7:3.5 (with the second part of the epoxy EpoTek 301B later added at 0.875). It is envisaged that the unset mixture may be spun in a centrifuge so as to promote settling of the tungsten particles towards an end of the backing element 424 which is proximate the piezoelectric element 418 in use.

The polysulfone of the main body 402 may be Sustason PSU rod stock produced from non UV-stabilised polysulphone resin (available from Rochling Sustaplast SE & Co. KG), which has a nominal acoustic impedance in the order of 2.78 MRayl. Due to the differential in acoustic impedance between the polysulfone and the piezoelectric material it is desirable to include an impedance matching layer. The piezo contact 420 is configured for this purpose. An ideal matching layer should have an acoustic impedance ($Z_0$) that is the square root of the product of the acoustic impedance of the adjacent materials (i.e. $Z_1$ and $Z_2$)—i.e. $Z_0=\sqrt{(Z_1 \cdot Z_2)}$. For the lead metaniobate piezoelectric material and polysulfone interface of the present example, the ideal acoustic impedance of the piezo contact 420 would be 6.67 MRayls. While it is generally preferable for the acoustic impedance of the matching layer to be as close as possible to the ideal value, in practice the impedance may be within a wider range and still produce a useful result—particularly where other design constraints are present.

The thickness of the piezo contact 420 is also designed to provide quarter wave matching with the ultrasound signal. More particularly, the thickness of the piezo contact 420 may be between 20 to 30% of the signal wavelength at the centre operating frequency of the transducer 400 (i.e. 3.75 MHz). As such, with a nominal acoustic impedance of about 6 MRayls and thickness of about 0.203 mm, the RO4003C piezo contact 420 is considered suitable for impedance matching. Further, the RO4003C material can be supplied with an electrodeposited copper foil, which is used in the exemplary embodiment to provide electrical contact between the piezo holder 414 and the bottom face of the piezoelectric element 418. In the exemplary embodiment the electrodeposited foil is 35 µm thick.

Figure 5:
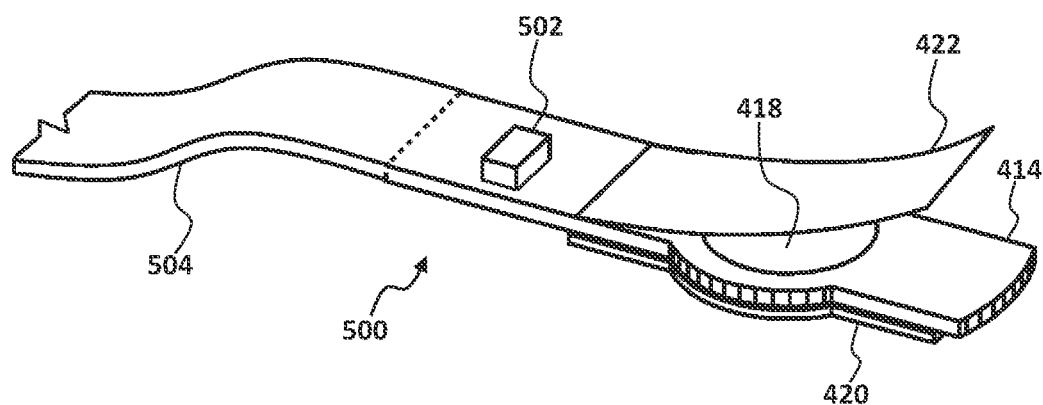
FIG. 5 is a perspective view of an exemplary piezoelectric assembly of the ultrasound transducer according to one aspect of the present disclosure.

FIG. 5 illustrates a piezoelectric assembly 500, including the piezo holder 414, piezoelectric element 418, piezo contact 420, and foil strip 422 as previously described. In an exemplary embodiment, prior to assembly of the transducer 400, the piezo contact 420 may be soldered to the piezo holder 414, and one end of the foil strip 422 soldered to the piezo holder 414. One or more electronic components 502 may also be soldered to the piezo holder 414. It may be seen that the piezo holder 414 also includes a flex portion 504—which may be used to provide electric connections to associated circuitry. The resulting sub-assembly is used to assist in assembly of the transducer 400.

During assembly, the piezoelectric element 418 is inserted into the aperture 416 of the piezo holder 414, beneath the foil strip 422. The thickness of the piezo holder 414 is such that the piezoelectric element 418 projects above it, to ensure contact with the foil 422 (and therefore backing element 424). The piezoelectric assembly 500 is then inserted into the slotted portion 412 of the main body 402. The slotted portion 412 and piezoelectric assembly 500 are shaped such that the piezoelectric element 418 is centred over the shaft 430 of the main body 402.

During assembly, an epoxy adhesive (for example, Scotch-Weld™ Epoxy Adhesive EC-2216 B/A available from 3M Company) is used between the piezoelectric element 418, the piezo contact 420 and the foil strip 422 for good acoustic contact, and between the piezo contact 420 and the main body 402, and between the foil strip 422 and the backing element 424.

The backing element 424 is inserted into the slotted portion 412, contacting the top of the foil strip 422. The cap 404 is then screwed on to the main body 402 until a specified torque is achieved, to squeeze the epoxy from between the various layers and provide a desired pressure as the epoxy sets. It is envisaged that the residual epoxy may be sufficiently thin so as to have a negligible effect on acoustic transmission properties or electrical contact. During assembly a fillet of epoxy is also applied to cover the electronic component 502 and portions of the piezo holder 414 adjacent the housing, to seal and encapsulate the transducer components.

Figure 6:
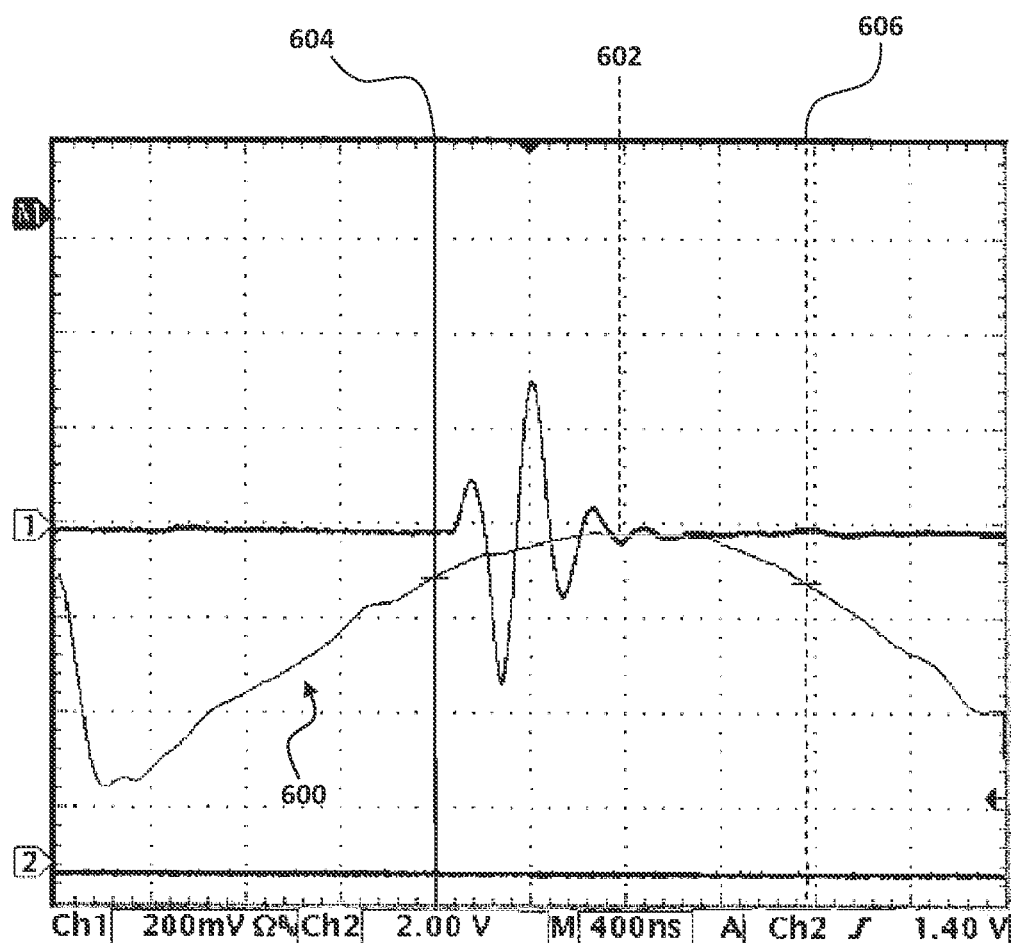
FIG. 6 is a graph of the frequency response of an exemplary ultrasound transducer according to one aspect of the present disclosure.

FIG. 6 illustrates the frequency response 600 of an exemplary ultrasound transducer 400 constructed in accordance with the description above. The ultrasound transducer 600 has a centre frequency 602 of about 3.75 MHz, with a lower −6 dB frequency limit 604 of about 2.5 MHz and an upper −6 dB frequency limit 606 of about 4.9 MHz. This provides a −6 dB bandwidth of about 2.4 MHz, which may be expressed as a −6 dB percentage bandwidth of about 64%. For completeness, it will be appreciated that variation in the tested bandwidth may be expected between different batches of the transducer, and between individual examples of the transducer design.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. Reference to any prior publications in this specification is not, and should not be taken as, an acknowledgement or any form of suggestion that that prior art forms part of the common general knowledge in the field of endeavour in any country in the world.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". The entire disclosures of all applications, patents and publications cited above and below, if any, are herein incorporated by reference.

The invention may also be said broadly to consist in the parts, elements and features referred to or indicated in the specification of the application, individually or collectively, in any or all combinations of two or more of said parts, elements or features.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

Aspects of the present invention have been described by way of example only and it should be appreciated that modifications and additions may be made thereto without departing from the scope thereof.

The invention claimed is:

1. An ultrasonic transducer including:
a piezoelectric element, wherein the piezoelectric element has an acoustic impedance of between 15 to 22 MRayls;
a fluid medium contact layer, wherein the fluid medium contact layer is a polymer layer;
a matching layer between the piezoelectric element and the fluid medium contact layer, wherein the matching layer has an acoustic impedance of between 4 to 10 MRayls; and
a backing layer, wherein the backing layer has an acoustic impedance of between 15 to 20 MRayls.

2. The ultrasonic transducer of claim 1, wherein the piezoelectric element is a lead metaniobate piezoelectric element.

3. The ultrasonic transducer of claim 1, wherein the polymer layer is polysulfone.

4. The ultrasonic transducer of claim 1, wherein the thickness of the fluid medium contact layer is configured to delay reflections of an acoustic signal from an interface between the fluid medium contact layer and a fluid in contact with the fluid medium contact layer by a predetermined number of wavelengths, or part wavelengths, of the acoustic signal.

5. The ultrasonic transducer of claim 4, wherein the thickness of the fluid medium contact layer is greater than two wavelengths of the acoustic signal.

6. The ultrasonic transducer of claim 1, wherein the matching layer is a hydrocarbon ceramic laminate layer.

7. The ultrasonic transducer of claim 1, wherein the matching layer has an acoustic impedance of between 5 to 8 MRayls.

8. The ultrasonic transducer of claim 1, wherein the thickness of the matching layer is configured to provide quarter wave matching with the acoustic signal.

9. The ultrasonic transducer of claim 8, wherein the thickness of the matching layer is between 0.2 to 0.3 wavelengths of the acoustic signal at the centre frequency of the ultrasonic transducer.

10. The ultrasonic transducer of claim 1, wherein the matching layer is a circuit board layer.

11. The ultrasonic transducer of claim 10, wherein the circuit board layer provides electrical connections to the piezoelectric element.

12. The ultrasonic transducer of claim 1, wherein the backing layer has an acoustic impedance substantially that of the piezoelectric element.

13. The ultrasonic transducer of claim 1, wherein at least one of the following is true:
the backing layer is a tungsten composite layer;
the tungsten composite of the tungsten composite layer includes first tungsten particles of a first size, and second tungsten particles of a second size;
the first tungsten particles are a granulated tungsten powder, and the second tungsten particles are a fine tungsten powder;
a ratio of granulated tungsten powder to fine tungsten powder in the tungsten composite is about 56:7;
the backing layer comprises a graduation in density of the first tungsten particles and the second tungsten particles; and
any combination thereof.

14. The ultrasonic transducer of claim 1, wherein the ultrasonic transducer has a centre frequency of one of: between 1 to 10 MHz, between 3 to 5 MHz, 3.5 to 4 MHZ, and about 3.75 MHz.

15. The ultrasonic transducer of claim 1, wherein the ultrasonic transducer has a −6 dB percentage bandwidth greater than 60%.

16. The ultrasonic transducer of claim 1, wherein the −6 dB bandwidth is between 2 to 3 MHz.

17. The ultrasonic transducer of claim 1, wherein at least one of the following is true:
the ultrasonic transducer further includes a housing having a main body, wherein a portion of the main body provides the fluid medium contact layer;
the main body includes a projection through which an acoustic pathway of the ultrasonic transducer passes;
the ultrasonic transducer further includes a piezoelectric assembly, the piezoelectric assembly including the piezoelectric element and the matching layer;
the piezoelectric assembly includes an element holder having an aperture in which the piezoelectric element is located;
wherein the element holder is made of a circuit board material;
the matching layer spans the aperture of the element holder;
the piezoelectric assembly includes an electrical contact on an opposing side of the piezoelectric element from the matching layer;
the main body includes a slotted portion configured to receive the piezoelectric assembly, wherein the ultrasonic transducer further includes a cap configured to be secured to the main body to hold the piezoelectric assembly in place within the slotted portion; and
any combination thereof.

18. A system for analysing a fluid, including:
- a ultrasound sensor device comprising an ultrasonic transducer as claimed in claim 1,
- a sample delivery device configured to deliver a sample of fluid from a fluid carrying and/or storing system to the ultrasound sensor device; and
- at least one processor configured to determine a characteristic of the sample of fluid based at least in part on a signal output from the ultrasound sensor device.

19. The system of claim 18, wherein the fluid is one of: a liquid, a solution including a liquid, and milk.

20. An ultrasound sensor device, including:
- an elongate hollow body configured to receive a fluid to be analysed;
- a first ultrasound transducer, provided at a first end of the hollow body, wherein the first ultrasound transducer includes:
  - a piezoelectric element, wherein the piezoelectric element has an acoustic impedance of between 15 to 22 MRayls;
  - a fluid medium contact layer, wherein the fluid medium contact layer is a polymer layer;
  - a matching layer between the piezoelectric element and the fluid medium contact layer,
  - wherein the matching layer has an acoustic impedance of between 4 to 10 MRayls; and
  - a backing layer, wherein the backing layer has an acoustic impedance of between 15 to 20 MRayls.

21. The ultrasound sensor device of claim 20, further including a second ultrasound transducer of the same configuration as the first ultrasound transducer, wherein the second ultrasound transducer is provided at a second end of the hollow body and facing the first ultrasound transducer.

22. The ultrasound sensor device of claim 21, wherein a length of the respective fluid medium contact layers of the first ultrasound transducer and the second ultrasound transducer is less than 15% of the overall path length.

23. The ultrasound sensor device of claim 21, wherein a path length between the respective piezoelectric elements of the first ultrasound transducer and the second ultrasound transducer is one of: greater than about 25 mm, between 25 mm to 100 mm, and about 70 mm.

24. The ultrasound sensor device of claim 20, wherein the hollow body is made of a metal.

25. The ultrasound sensor device of claim 20, wherein the hollow body comprises an acoustically reflective surface, wherein the first ultrasound transducer faces the acoustically reflective surface.

26. The ultrasound sensor device of claim 25, wherein a total return path length between the piezoelectric element of the first ultrasound transducer and the acoustically reflective surface is one of: greater than about 25 mm, between 25 mm to 100 mm, and about 70 mm.

* * * * *